United States Patent
Toledo-Crow et al.

(10) Patent No.: US 9,554,857 B2
(45) Date of Patent: Jan. 31, 2017

(54) APPARATUS, SYSTEM AND METHOD FOR PROVIDING LASER STEERING AND FOCUSING FOR INCISION, EXCISION AND ABLATION OF TISSUE IN MINIMALLY-INVASIVE SURGERY

(75) Inventors: Ricardo Toledo-Crow, New York, NY (US); Snehal Patel, New York, NY (US); Milind Rajadhyaksha, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 13/420,340

(22) Filed: Mar. 14, 2012

(65) Prior Publication Data

US 2012/0302828 A1 Nov. 29, 2012

Related U.S. Application Data

(63) Continuation-in-part of application No. PCT/US2010/048807, filed on Sep. 14, 2010.
(Continued)

(51) Int. Cl.
*A61N 5/067* (2006.01)
*A61B 18/24* (2006.01)
*A61B 18/22* (2006.01)

(52) U.S. Cl.
CPC ........ *A61B 18/24* (2013.01); *A61B 2018/2277* (2013.01); *A61B 2018/2283* (2013.01); *A61B 2018/2294* (2013.01)

(58) Field of Classification Search
CPC ............ A61B 18/24; A61B 2018/2294; A61B 2018/2283; A61B 2018/2277; B23K 26/14; B23K 26/16; B23K 26/08; B23K 26/10
(Continued)

(56) References Cited

U.S. PATENT DOCUMENTS 4,822,974 A * 4/1989 Leighton ............ B23K 26/0652
219/121.67
4,913,142 A 4/1990 Kittrell et al.
(Continued)

FOREIGN PATENT DOCUMENTS

GB 2489286 12/2007
JP 2008-529682 2/2006
(Continued)

OTHER PUBLICATIONS

International Search Report for International Application No. PCT/US2010/048807.
(Continued)

*Primary Examiner* — William Thomson
*Assistant Examiner* — Victor Shapiro
(74) *Attorney, Agent, or Firm* — Stroock & Stroock & Lavan, LLP.

(57) ABSTRACT

Exemplary embodiments of apparatus, system, computer-accessible medium, procedure and method are provided which can be used for providing laser steering and focusing for, e.g., incision, excision and/or ablation of tissue in minimally-invasive surgery. For example, the exemplary apparatus can include at least one optical element which can be configured to refract and/or diffract light provided in a structure which can be configured to be inserted into a body, where at least one of the optical element(s) is structured to receive the light at a first angle and generate a refracted and/or diffracted light at a second angle which can be different from the first angle relative to an optical axis. For example, an actuating arrangement can be provided, which can be configured to control the optical element(s), can be provided and situated at least partially within the at least one structure.

7 Claims, 19 Drawing Sheets

Related U.S. Application Data

(60) Provisional application No. 61/242,202, filed on Sep. 14, 2009.

(58) Field of Classification Search
USPC   600/473, 476, 478, 142, 342, 160; 356/497, 356/511; 398/139; 606/12; 359/362, 359/371, 385; 385/131; 219/121.67, 219/121.8; 350/6.4, 287, 484
See application file for complete search history.

(56) References Cited

U.S. PATENT DOCUMENTS

| | | | |
|---|---|---|---|
| 5,163,936 A | | 11/1992 | Black et al. |
| 5,743,902 A | * | 4/1998 | Trost .................... A61B 18/203 606/11 |
| 5,786,924 A | * | 7/1998 | Black .................. A61B 18/203 359/197.1 |
| 5,814,042 A | * | 9/1998 | Zair ....................... A61B 18/20 359/202.1 |
| 6,152,918 A | | 11/2000 | Padilla et al. |
| 6,445,939 B1 | | 9/2002 | Swanson et al. ............. 600/342 |
| 6,529,543 B1 | | 3/2003 | Anderson et al. |
| 6,831,781 B2 | * | 12/2004 | Tearney et al. ............... 359/385 |
| 6,975,898 B2 | * | 12/2005 | Seibel ............................ 600/473 |
| 7,108,692 B2 | | 9/2006 | Frenz et al. |
| 7,220,255 B2 | * | 5/2007 | Lai ................................. 606/12 |
| 7,372,606 B2 | * | 5/2008 | Broome ................. B41J 2/471 359/216.1 |
| 7,448,995 B2 | | 11/2008 | Wiklof et al. |
| 7,578,786 B2 | * | 8/2009 | Boulais et al. .............. 600/142 |
| 7,662,147 B2 | * | 2/2010 | Kessler ................. A61F 9/0084 128/898 |
| 7,733,497 B2 | * | 6/2010 | Yun et al. ...................... 356/497 |
| 7,970,458 B2 | * | 6/2011 | Norris et al. .................. 600/478 |
| 8,360,963 B2 | * | 1/2013 | Hendriks et al. ............. 600/160 |
| 2001/0048077 A1 | | 12/2001 | Afanassieva |
| 2003/0011782 A1 | * | 1/2003 | Tanno .......................... 356/497 |
| 2004/0073120 A1 | * | 4/2004 | Motz et al. .................... 600/478 |
| 2006/0195076 A1 | | 8/2006 | Blumenkranz et al. |
| 2006/0244973 A1 | * | 11/2006 | Yun et al. ...................... 356/511 |
| 2007/0133935 A1 | * | 6/2007 | Fine .............................. 385/131 |
| 2007/0188855 A1 | * | 8/2007 | Shishkov et al. ............. 359/362 |
| 2008/0013960 A1 | * | 1/2008 | Tearney et al. ............... 398/139 |
| 2008/0088901 A1 | * | 4/2008 | DeBenedictis .... G02B 26/0875 359/212.1 |
| 2008/0304143 A1 | * | 12/2008 | Jacobsen et al. ............. 359/371 |
| 2009/0095721 A1 | * | 4/2009 | Scaggs ................. G02B 26/101 219/121.67 |
| 2009/0187176 A1 | * | 7/2009 | Assa ...................... A61B 18/22 606/17 |

FOREIGN PATENT DOCUMENTS

| | | |
|---|---|---|
| JP | 2008-529682 A | 8/2008 |
| RU | 2163790 C1 | 3/2001 |
| WO | WO 02/09609 A1 | 2/2002 |
| WO | WO 2006088993 A2 | 8/2006 |

OTHER PUBLICATIONS

International Written Opinion for International Application No. PCT/US2010/048807.
Second Office Action for Mexican Application No. MX/a/2012/003156 mailed on Oct. 30, 2014.
First Office Action for Eurasian Patent Application No. 201270426 mailed on May 27, 2014.
First Office Action for Chinese Patent Application No. 201080046711.2 mailed on Jul. 3, 2014.
Final Office Action for Japanese Application No. 2012-528994 mailed on Mar. 31, 2015.
Office Action for Eurasian Application No. 201270426 mailed on Feb. 20, 2015.
Office Action for Mexican Application No. MX/a/2012/003156 mailed on Apr. 16, 2015.
Office Action for Chinese Application No. 201080046711.2 mailed on May 6, 2015.
Office Action for European Application No. 10816285 mailed on Aug. 8, 2015.
Office Action for Mexican Patent Application No. MX/a/2012/003153 mailed on Nov. 10, 2015.
Office Action for Japanese Patent Application No. 2012-528994 mailed on Jan. 12, 2016.
Office Action for Canadian Patent Application No. 2,773,984 mailed on Feb. 15, 2016.
Office Action for New Zealand Patent Application No. 625085 mailed on Feb. 17, 2016.
Office Action for New Zealand Patent Application No. 625085 mailed on Nov. 12, 2015.
Office Action for Mexican Patent Application No. MX/a/2014/012231 mailed on Nov. 18, 2015.
Office Action for Chinese Patent Application No. 201080046711.2 mailed on Dec. 2, 2015.
Office Action for Mexican Patent Application No. MX/a/2014/012232 mailed on Nov. 18, 2015.

* cited by examiner

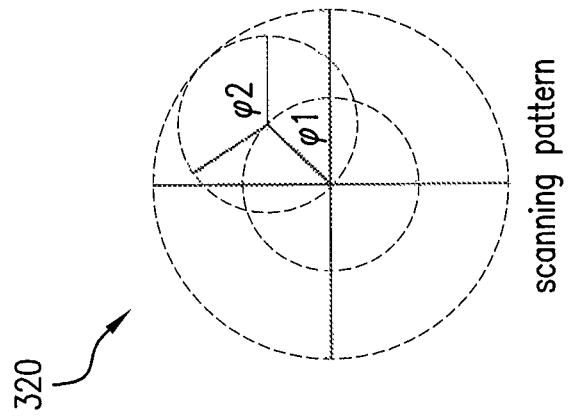
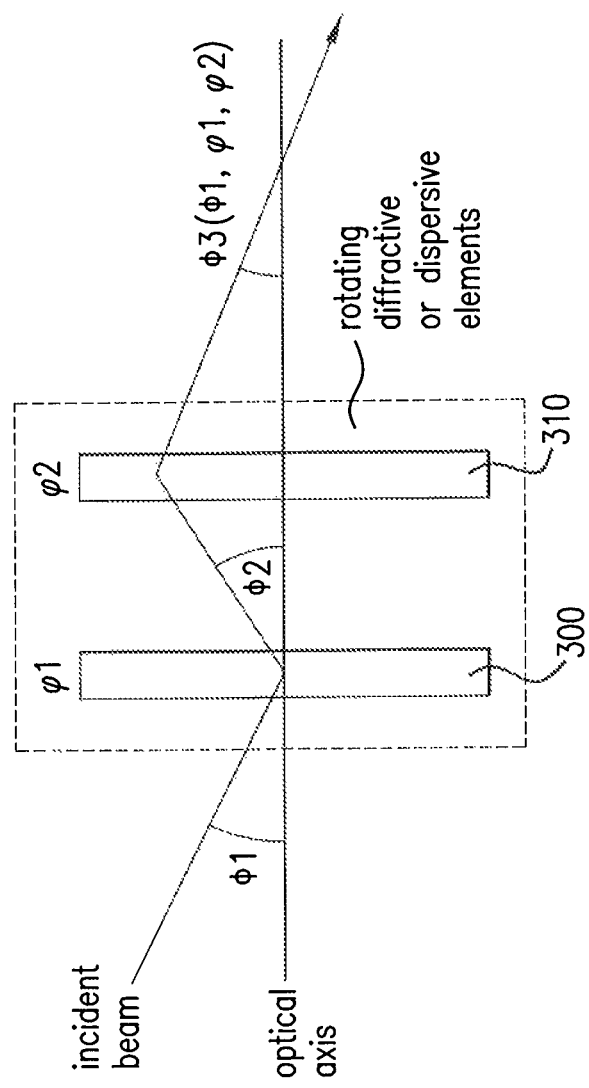

2 wedges with gap σ

2 wedges without gap

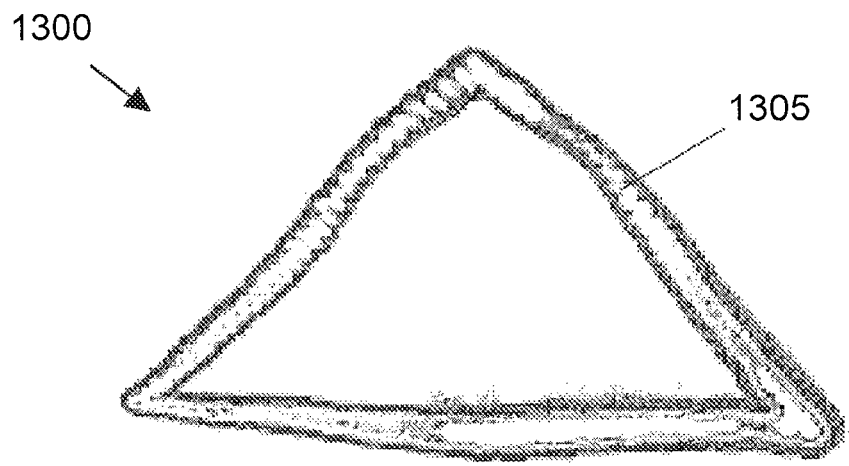
FIG. 13A
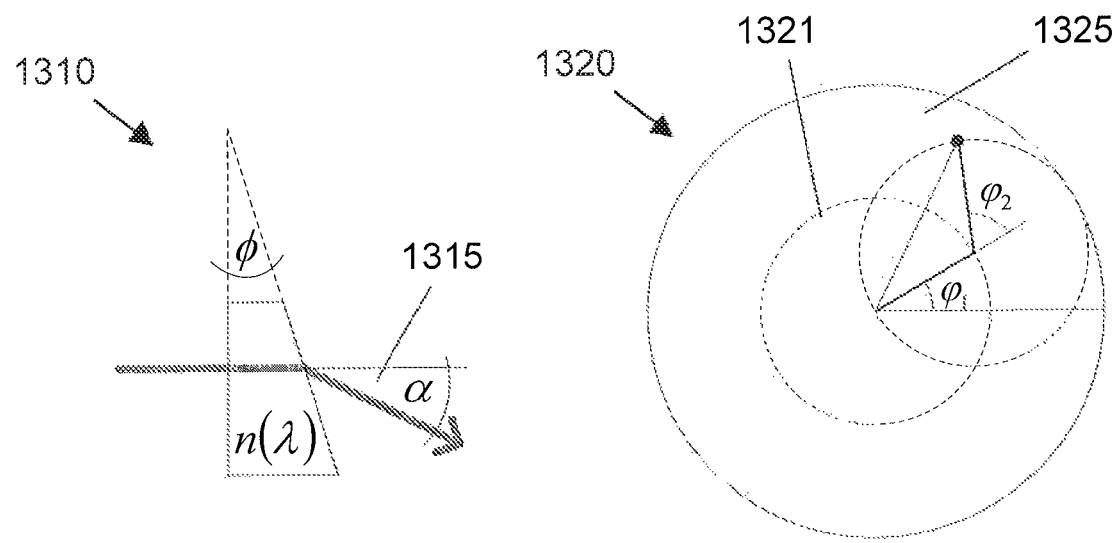
FIG. 13B
FIG. 13C

APPARATUS, SYSTEM AND METHOD FOR PROVIDING LASER STEERING AND FOCUSING FOR INCISION, EXCISION AND ABLATION OF TISSUE IN MINIMALLY-INVASIVE SURGERY

CROSS-REFERENCE TO RELATED APPLICATION(S)

This application is a continuation-in-part application of International Application PCT/US2010/048807 filed on Sep. 14, 2010. The present application also relates to and claims priority from U.S. Patent Application No. 61/242,202 filed Sep. 14, 2009. Accordingly, the entire disclosures of such applications are hereby incorporated herein by reference.

FIELD OF THE DISCLOSURE

The present disclosure relates generally to apparatus, system and method for providing laser facilitating incision, excision and/or ablation of tissue in minimally-invasive surgery.

BACKGROUND INFORMATION

Minimally invasive surgical techniques can offer the potential for reliable cancer control with minimal impact on post treatment function of the diseased organ. There have been certain advances in providing instrumentation for minimally invasive surgery of many diseases. Although the use of $CO_2$ lasers has become well established and can be considered to be as effective and precise scalpel, it is likely still largely limited to operations where the surgeon has unobstructed access to the tissue. (See, e.g., Polanyi, Bredemei. Hc et al. 1970; Jako 1972; Mihashi, Jako et al. 1976; Garden, Obanion et al. 1988). A particular advantage of the $CO_2$ laser over other lasers can be that it can be readily absorbed by water, which is the primary component of most biological tissues. This can facilitate minimal thermal spread and injury to adjoining normal tissue, making the $CO_2$ laser especially useful for surgery near critical anatomical structures, for example.

The $CO_2$ laser can also be used to seal small blood vessels and lymphatics, likely minimizing bleeding and risk of lymphatic metastases from tumors. With the appropriate surgical optics, the tissue interaction of the $CO_2$ laser can be used advantageously for a precise excision of a tumor with minimal injury to normal tissue so as to likely preserve function without compromising the cure. However, an exemplary disadvantage of the $CO_2$ laser can be related to its beam's likely inability to travel in any medium other than air. Since the $CO_2$ laser beam is likely unable to be transmitted along glass or conventional optical fibers, its use has probably been generally restricted to "line-of-sight" applications, in which it can be passed down a hollow, air-filled, straight rigid instrument or endoscope. Thus, endoscopic applications of this technique and the $CO_2$ laser has likely been restricted to treatment of tumors of the mouth, pharynx, larynx and cervix, for example.

Further, a delivery of any type of surgical laser light into a body cavity by means fiber optics has likely been limited to use in the near field, e.g., by bringing the distal tip of the fiberoptic close to the tissue in order to keep the power density high. It can be very difficult to facilitate a flexible, variable and accurate maneuvering of such laser beam.

Instrumentation for endoscopic applications of the $CO_2$ lasers and other surgical lasers has undergone refinement and improvement, but access to the larynx and pharynx in certain patients with adverse anatomic features has likely continued to pose a problem. This limitation of the conventional technology can be largely responsible for the potential benefits of certain surgery being denied to a large number of patients, such as patients whose tumors can be relatively difficult to access for surgical resection with endoscopic $CO_2$ laser instrumentation, for example. Consequently, many of these patients have been treated using non-surgical options, including radiation with or without chemotherapy, to avoid the potentially devastating effects that conventional surgery can have on a patient's quality of life. However, the use of such non-surgical "organ preserving" approaches can likely often cause permanent and significant side effects that can drastically alter the lives of patients who survive after treatment.

Currently, one of the more widely used delivery methods for the $CO_2$ lasers (and other lasers) in surgery is likely a "line-of-sight" system that may include a laser source that can deliver energy to a micromanipulator coupled to an operating microscope via an articulated arm. For example, a hollow core fiber optic delivery systems for $CO_2$ surgical lasers which can facilitate providing a laser beam into a confined space has been described by Hart Temelkuran et al. (See, e.g., Temelkuran, Hart et al. 2002). As described, the fiber can transmit the light from the laser source to its distal end that can be used as a "laser scalpel." However, the use of the fiber delivery techniques are likely not ideal as they can have some of the limitations of line-of-sight technologies. Additionally, fiber delivery techniques can introduce certain other problems.

For example, similarly to line-of-sight delivery techniques, it can be important to externally manipulate an apparatus using fiber delivery techniques if it is to be used in confined spaces. Additionally, because the laser beam exiting the fiber can rapidly diverge, the fiber likely should be precisely placed near the tissue in order to incise or ablate the tissue. If the fiber is placed too far away (e.g., over one millimeter), the power density can likely drop, and the laser scalpel can become ineffective. However, if the fiber tip touches the tissue, it can burn and/or become obstructed. Further, a precise manipulation of the working end of the fiber inside a body cavity can be challenging for the endoscopic surgeon due to the difficulty of maintaining a consistent depth of incision with the laser directed through a hand held fiber moving over an uneven tissue surface in a confined closed space. Moreover, a complex electro-mechanical system should likely need to be provided for the laser beam to be controlled remotely.

Certain scanners having dimensions that can likely be appropriate for endoscopic use have been described. (See, e.g., Fountain and Knopp 1992; Dohi, Sakuma et al. 2003; Wu, Conry et al. 2006; and Tsia, Goda et al. 2009). Many of these devices can be instruments that have likely been initially designed specifically for endoscopic imaging, and only subsequently were considered for use in performing tissue modification and altered to accordingly. However, the technical requirements of imaging scanners and surgical laser scanners are generally not the same, but rather can be very different. While imaging scanners generally can require regular scanning patterns to generate the image, surgical laser scanners generally can utilize random and precise variations of the scanners to address the discrete adjacent and distant points that can be involved in a typical laser surgery pattern. Thus, conventional apparatuses provided for surgery are described as having the optics and mechanical control of the scanners external to the body. (See, e.g., Fountain and Knopp 1992). Endoscopic devices have been described with optics designed to be inserted into the body, but with the mechanical control external to the body. (See, e.g., Dohi, Sakuma et al. 2003; Wu, Conry et al. 2006). These systems have certain limitations and associated problems such as spatial and temporal inaccuracies associated with the remote transmission of positioning forces from the external motors to the internal optics. Additionally, an imaging apparatus can be provided that can be used for laser surgery, in principle, purportedly without mechanical movements and that can be internalized. (See, e.g., Tsia, Goda et al. 2009). However, this device requires a tunable laser, and thus would likely not be able to work with surgical lasers like a $CO_2$ laser, for example.

Accordingly, there may be a need to address and/or overcome at least some of the above-described deficiencies and limitations, and to provide exemplary embodiments of arrangement and method according to the present disclosure as described in further detailed herein.

SUMMARY OF EXEMPLARY EMBODIMENTS OF THE DISCLOSURE

Indeed, one of the objects of certain exemplary embodiments of the present disclosure can be to address the exemplary problems described herein above, and/or to overcome the exemplary deficiencies commonly associated with the prior art as, e.g., described herein. Accordingly, for example, provided and described herein are certain exemplary embodiments of exemplary apparatus, system, procedure and method according to the present disclosure which can be used for providing laser steering and focusing for incision, excision and/or ablation of tissue in minimally-invasive surgery.

According to one exemplary embodiment of the present disclosure, an exemplary apparatus is provided that can include at least one optical element which can be configured to refract and/or diffract light provided in at least one structure which can be configured to be inserted into a body, where at least one of the optical element(s) is structured to receive the light at a first angle and generate a refracted and/or diffracted light at a second angle which can be different from the first angle relative to an optical axis (e.g., the straight line which passes through the center of the optical element).

In a particular exemplary embodiment of the present disclosure, an exemplary actuating arrangement can be provided which can be configured to control at least one of the optical element(s) to change the second angle of the refracted and/or diffracted light can also be provided and situated at least partially within the at least one structure, for example. The at least one light can be a laser light, and the second angle can be uniform. At least two of the optical elements can be structured to generate the refracted and/or diffracted light.

According to certain exemplary embodiments of the present disclosure, at least one of the exemplary element(s) can be a wedge or prism, and/or a grating, such as a grating of variable spatial frequency, an acoustooptical grating, a fixed grating, a holographic transmission grating, a blazed grating, etc. The exemplary arrangement can be further configured to control at least one of the optical element(s) to change the second angle of the refracted and/or diffracted light and a uniform third angle of the refracted and/or diffracted light which is different from the uniform second angle. The exemplary actuating arrangement can be controlled manually, mechanically, electrically, electromechanically and/or remotely. For example, the exemplary actuating arrangement can be controlled at least partially by a mechanical and/or an electromechanical arrangement.

An exemplary fiber optic configuration which can be configured to provide the at least one light therethrough can also be provided in accordance with certain exemplary embodiments of the present disclosure. For example, the exemplary fiber optic configuration can be configured to deliver the light to at least one of the optical element(s). At least one lens which is optically associated with at least one of the optical element(s) can further be provided, such as in an optical path between the optical elements, between the optical element(s) and the fiber optic configuration or after the optical element(s).

According to certain exemplary embodiments of the present disclosure, a further arrangement can be provided which can be configured to provide the laser light and which can be controlled so as to modify a depth of a delivery of the refracted and/or diffracted light to a target tissue in the exemplary structure(s). For example, the further arrangement can include an ablation laser, an incision laser and/or an excision laser. A receiving arrangement can also be provided which can be structured to be provided in the body and configured to receive at least one further light, such as a visual light, from a target tissue in the exemplary structure(s). For example, the receiving arrangement can include at least one light detector, which can be a charged-coupled device (CCD), a fiberoptic bundle and/or a complementary metal oxide semiconductor (CMOS) detector, for example, and be configured to provide at least one image of the target tissue.

Further, an additional arrangement can be provided which can be configured to provide the further light to the target tissue and which can be structured to be situated within the body. A particular arrangement can also be provided which can facilitate a visual control of an application of the light by, e.g., (i) a user control and/or (ii) automatically. Additionally, an external configuration, which can be configured to deliver the light to the structure(s), can be provided and situated externally from the body. The external configuration can be further configured to provide multiple frequencies of the light sequentially in time and/or at the same time. For example, the external configuration can be or include a tunable laser arrangement.

According to certain exemplary embodiments of the present disclosure, at least one dispersive element can be provided which can be configured to deflect and/or refract the light at a particular wavelength dependent angle in a radial direction during a rotation of the dispersive element(s) to move the light in a rotational motion. For example, the external configuration can be configured to vary the wavelength of the light so as to move the light radially and/or to be rotated so as to move the light.

According to another exemplary embodiment of the present disclosure, an exemplary apparatus is provided that can include, inter alia, a plurality of optical elements which can be configured to reflect light, such as laser light, and which can be provided in at least one structure which can be configured to be inserted into a body. For example, a first configuration of the optical elements can be positioned or controlled to receive the light at a first angle and generate a first reflected light at a second angle which can be different from the first angle relative to an optical axis. A second configuration of the optical elements can be structured to receive the first reflected light and generate a second reflected light at a third angle which can be different from the second angle relative to the optical axis.

An actuating arrangement which can be configured to control the first configuration and/or the second configuration of the optical elements to change the second angle and/or the third angle of the light can also be provided and situated at least partially within the structure(s). A third configuration of the optical elements can be structured and/or controlled to receive the second reflected light and generate a third reflected light at a fourth angle which can be different from the third angle relative to the optical axis. A fourth configuration of the optical elements can be structured and/or controlled to receive the third reflected light and generate a fourth reflected light toward the body at a fifth angle which is different from the fourth angle relative to the optical axis. The actuating arrangement can be further configured to control at least one of the optical elements to change the second angle of the reflected light and the third angle of the reflected light relative to the optical axis, wherein the first and/or second angles can be uniform. The actuating arrangement can be controlled at least one of manually, mechanically, electrically, electromechanically or remotely, such as at least partially by a mechanical arrangement, for example.

The second configuration can be further structured to generate the second reflected light so as to have a cylindrical shape. The first configuration and/or the second configuration can be or include at least one section which can have a conical shape. For example, the first configuration can be or include a conical mirror, and the second configuration can be or include a conical section mirror. The third configuration and/or the fourth configuration can be or include at least one section which can have a parabolic shape. For example, the third configuration can be or include a parabolic section mirror, and the fourth configuration can be or include a parabolic mirror.

According to yet another exemplary embodiment of the present disclosure, provided is an exemplary process for providing laser steering and focusing, which can include, inter alia, defining a pattern to irradiate at least one section in a body, and controlling at least one optical element provided in a housing to refract and/or diffract at least one light based on the pattern using an actuating arrangement. The housing can be structured to be inserted into the body, and/or the actuating arrangement can be structured to be inserted into a body.

The exemplary process can also include, inter alia, providing the light, controlling at least one of the optical elements to change an angle of the refracted and/or diffracted light and controlling the at least one light so as to modify a delivery of the refracted and/or diffracted light to a target tissue in the structure(s). According to certain exemplary embodiments of the present disclosure, the exemplary process can further include, inter alia, monitoring at least one position and/or orientation of at least one of the optical elements or the refracted and/or diffracted light, generating at least one signal based on the position and/or the orientation, and controlling the position and/or the orientation of at least one of the optical elements based on signal(s).

According to still yet another exemplary embodiment of the present disclosure, provided is an exemplary computer-accessible medium, which can be non-transitory, and which can have stored thereon computer executable instructions for providing laser steering and focusing, which, when executed by a hardware processing arrangement, configure the hardware processing arrangement to perform certain procedures, such as, e.g., defining a pattern to irradiate at least one section in a body, and controlling at least one optical element provided in a housing to refract and/or diffract at least one light based on the pattern using an actuating arrangement. The housing and/or the actuating arrangement can be structured to be inserted into the body.

The exemplary processing arrangement can be further configured to control a source arrangement to provide the at least one light, to control at least one of the optical elements to change an angle of refracted and/or diffracted light with respect to the optical axis, and/or control a source arrangement by modifying at least one characteristic of the light so as to modify a position of a delivery of the refracted and/or diffracted light to a target location in the body. Additionally, according to certain exemplary embodiments of the present disclosure, the exemplary processing arrangement can be further configured to monitor a position and/or orientation of at least one of the optical elements or the refracted and/or diffracted light, generate at least one signal based on the position and/or the orientation, and control the position and/or the orientation of at least one of the optical elements based on the signal(s).

According to still yet another exemplary embodiment of the present disclosure, an exemplary process can be facilitated for steering and/or focusing a laser on or to a target tissue within a body, which can include, inter alia, locating the target tissue within the body from a position within the body and establishing a position of the device relative to the target tissue using a particular arrangement that has a housing that is inserted into the body. The exemplary process can also include generating control data by tracing over an image of the tissue a path to be cut with at least one electro-magnetic radiation, defining an area to be effected by the at least one electro-magnetic radiation, and/or controlling the position of the at least one electro-magnetic radiation in real time. Further, the exemplary process can include, with at least one actuating arrangement provided in the housing, controlling at least one optical element provided in the housing, based on the control data, to refract and/or diffract at least one light. The at least one light can be a laser light, and the path can be based on a predetermined pattern.

According to still yet another exemplary embodiment of the present disclosure, an exemplary computer-accessible medium can be provided, which can be non-transitory, and which can have stored thereon computer executable instructions for steering and/or focusing a laser on or to a target tissue within a body, which, when executed by a hardware processing arrangement, configure the hardware processing arrangement to perform certain procedures, such as, e.g., locating the target tissue within the body from a position within the body and establishing a position of the device relative to the target tissue using a particular arrangement that has a housing that is inserted into the body. The exemplary procedure executed using the computer-executable instructions can further include generating control data by tracing over an image of the tissue a path to be cut with at least one electro-magnetic radiation, defining an area to be effected by the at least one electro-magnetic radiation, and/or controlling the position of the at least one electro-magnetic radiation in real time. Further, the exemplary instructions can configure the processing arrangement to with at least one actuating arrangement provided in the housing, control at least one optical element provided in a housing, based on the control data, to at least one of refract or diffract at least one light, for example. The at least one light can be a laser light, and the path can be based on a predetermined pattern.

According to another exemplary embodiment of the present disclosure, the light(s) can have a plurality of first beams, and the refracted or diffracted light(s) can have a plurality of second beams. For example, it is possible to use a first optical arrangement to provide the first beams to the optical element(s) at the first angle. It is also possible to use a second optical arrangement to receive the second beams at the second angle, and converge the second beams.

In still another exemplary embodiment of the present disclosure, it is possible to utilize a light propagating arrangement to provide the light(s) toward the optical element(s) at the first angle. Further, an actuating arrangement can be utilized to control the light propagating arrangement to change a position thereof within the structure(s) to change the first angle. The actuating arrangement can include at least one magnet arrangement (or a plurality of magnets).

These and other objects, features and advantages of the exemplary embodiment of the present disclosure will become apparent upon reading the following detailed description of the exemplary embodiments of the present disclosure, when taken in conjunction with the appended claims.

BRIEF DESCRIPTION OF THE DRAWINGS

For a more complete understanding of the present disclosure and its advantages, reference is now made to the following description, taken in conjunction with the accompanying drawings, in which:

FIG. 3A is a side view of optical elements that can be included in the exemplary embodiment of the laser scanning endoscopic head illustrated in FIG. 2;

FIG. 3B is an illustration of an exemplary scanning geometry generated using the exemplary optical elements of FIG. 3A;

FIG. 13A is an exemplary image of an exemplary scanning pattern generated by a device or an arrangement in accordance with an exemplary embodiment of the present disclosure;

FIG. 13B is an illustration of an exemplary scanner geometry in accordance with yet another exemplary embodiment of the present disclosure;

FIG. 13C is an illustration of a further exemplary scanning pattern in accordance with an exemplary embodiment of the present disclosure;

Figure 1:
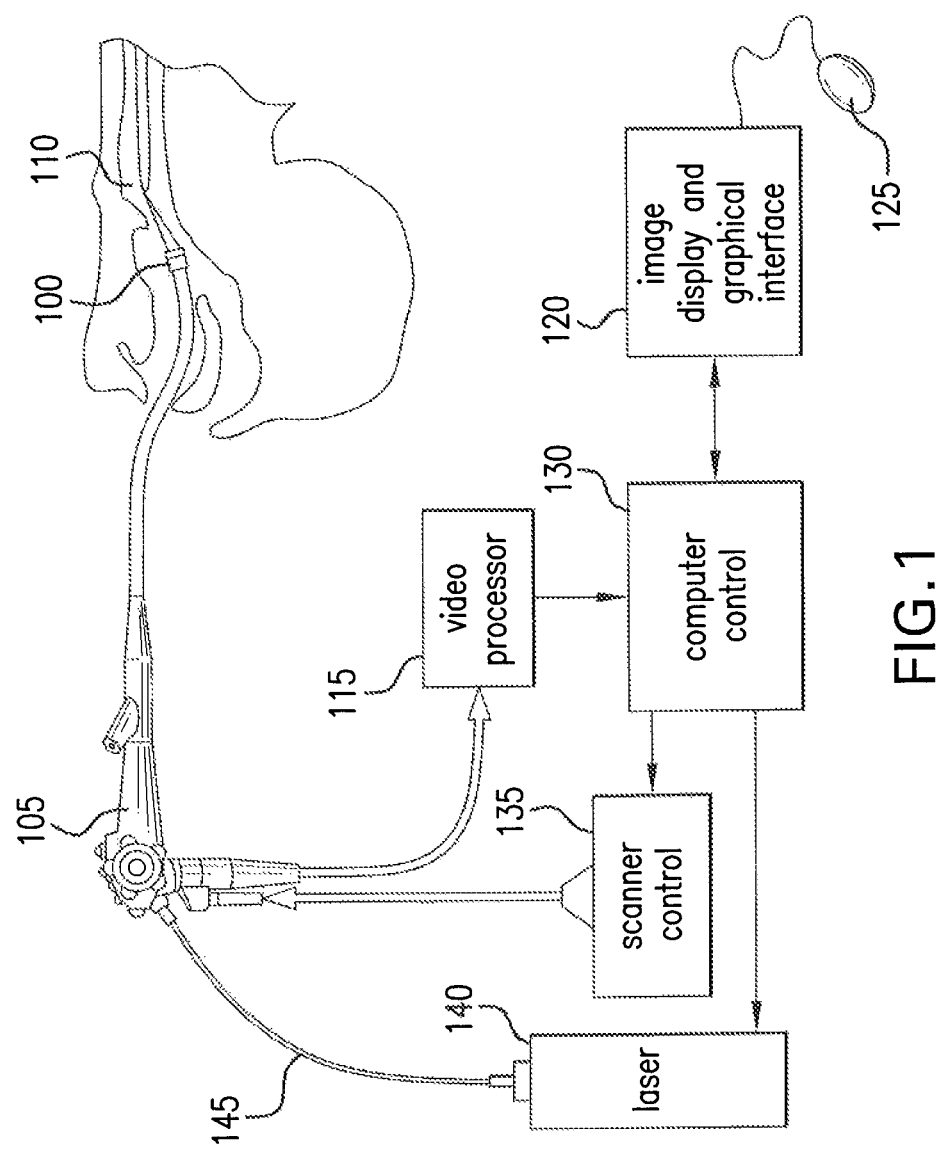
FIG. 1 is a diagram of an endoscopic laser scalpel system in accordance with an exemplary embodiment of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments and is not limited by the particular embodiments illustrated in the figures and the accompanying claims. It is intended that changes and modifications can be made to the described embodiments without departing from the true scope and spirit of the subject disclosure.

DETAILED DESCRIPTION OF EXEMPLARY EMBODIMENTS

To address and/or overcome at least some of the above-described deficiencies, exemplary embodiments of the device, arrangement, apparatus, non-transitory computer-accessible medium and method can be provided in according to the present disclosure. For example, it is possible to introduce into the body cavity a small exemplary scanner that can be controlled remotely by the surgeon to guide the laser. The laser can be delivered to the body cavity and scanned over the tissue using, e.g., two or more of small, rotating optical wedges. One of the advantages of using one exemplary prism arrangement, e.g., which can be referred to as a Risley prism pair, is that it can be made with a very small profile, e.g., not much larger than the diameter of the optical fiber (under 10 mm), and that it can be placed at the distal end of an endoscope. One or more lenses can be used to focus the light and improve the power density delivered to the tissue and/or adjust the depth of operation of the device. Using such exemplary embodiment of the arrangement/system can facilitate a precise manipulation of the laser delivered into relatively inaccessible body cavities by a flexible or rigid conduit. This exemplary embodiment can also be utilized with an articulated arm and/or a straight, line-of-sight laser delivery procedure/arrangement.

For example, an exemplary embodiment of the system can include an imaging device e.g., a video camera which can be provided next, near and/or fixed to the scanners to provide a live endoscopic image to the user (e.g., the surgeon), who can trace a graphic over the video to establish a particular scanning path on the image of the tissue. The path can then be translated into appropriate wedge movements to produce a scan with appropriate speed and trajectory on the tissue. Alternatively or in addition, the user can control the laser path and delivery directly through a pointer or joystick (or mouse, touch-screen, digital pen, track ball, etc.) from the video stream as displayed on a video monitor. The exemplary system can also be configured or structured to vary the focus of the beam on the tissue to accommodate different depths of operation, thus facilitating a real-time three-dimensional control of the laser in the body cavity.

An exemplary laser delivery using the exemplary embodiments of the devices, systems, apparatus, non-transitory computer-accessible medium and arrangements according to the present disclosure can be provided so as to implement and/or utilize multiple configurations. For example, it is possible to include one or more ducts and/or channels, including, e.g., a duct for a photonic bandgap, and/or a hollowcore fiber for the $CO_2$ laser delivery. It is also possible to include a direct, line-of-sight configuration for delivery of the laser and/or utilize an articulated arm delivery mechanism with certain exemplary systems according to the present disclosure. For example, exemplary configurations of the devices, systems, apparatus, non-transitory computer-accessible medium and arrangement according to the present disclosure can provide for depth adjustment to be performed by, e.g., moving a negative lens to control the focus. Certain exemplary configurations can be independent of some or all optical fibers. For example, certain exemplary embodiments of the devices, systems, apparatus, non-transitory computer-accessible medium and arrangement according to the present disclosure can utilize a variety of certain electro-magnetic radiation sources which can operate with some or all of the wavelengths that can be used in performing surgeries, including, e.g., Nd:YAG @ 1064 nm, Argon and Krypton Ion @ 488 nm, and 684 nm, etc.). Further, according to certain exemplary embodiments of the present disclosure, the endoscope head and body can be composed of biocompatible materials, which can facilitate relatively easy cleaning and sterilization, for example.

FIG. 1 shows a diagram of are endoscopic laser scalpel system in accordance with an exemplary embodiment of the present disclosure. The exemplary endoscopic laser scalpel system illustrated in FIG. 1 can include a laser scanning endoscopic head 100 mounted on the distal end of a laryngoscope or endoscope 105. Exemplary embodiments of a laser scanning endoscopic head of a laryngoscope or endoscope are further described herein with reference to FIGS. 2-11. An exemplary imaging device in the endoscopic head 100 can relay a still, live or moving endoscopic image of the tissue in a body cavity 110 through a video stream to a processor 115 that can display the image, e.g., in a user-readable format on a monitor and/or screen 120. A user (e.g., a surgeon) can utilize an input device 125, which can be a graphical input device (e.g., mouse, joystick, touch screen, digital pen, track ball, etc.), that can be used to overlay the live image with a graphical representation of the path of a desired laser cut. A computer control arrangement 130 can be programmed and/or activated to convert Cartesian coordinates of a graphic path on the display into angular coordinates for a scanner that can be sent to a scanner control 135. The scanner control 135 can transform the coordinates into electrical command signals that can be transmitted to the motors in an endoscopic head 100. The scanner control 135 can also activate a laser 140 and control the laser light intensity delivered to the scanners through an optical fiber 145 or another laser delivery system, for example.

According to certain exemplary embodiments of the present disclosure, the motors can be activated in response to the movement of the graphical input device in real time, to provide direct control of the scanners by the user, for example. It is also possible to utilize a rigid operating laryngoscope instead of a flexible endoscope, such as the endoscope 105. As shown in FIG. 1, the exemplary system according to the present disclosure can include an electrooptical attenuator that can be controlled by a computer control, such as computer control 130, and used to modulate the intensity of a laser (e.g., laser 140). The optical fiber 145 can be a single mode optical fiber. Alternatively, optical fiber 145 can be a multi mode optical fiber. Further, for example, optical fiber 145 can be a hollowcore or photonic bandgap optical fiber. In accordance with certain exemplary embodiments of the present disclosure, direct delivery of the laser, or delivery of the laser through an articulated arm, to the endoscopic scanning head 100 can be used in conjunction with or instead of using the optical fiber 145. It is also possible to use a radio frequency (or radio frequencies, including a band thereof) to interface the scanner control unit 135 with a local processor located in the scanning head 100. Additionally, it is possible to use a local source of power, such as a battery, that can be located in (or near) the scanning head 100 to provide power to operate the device. Further, it is possible to incorporate or include the laser source 140 into or within the endoscopic scanning head 100. Thus, in accordance with certain exemplary embodiments of the present disclosure, it is possible to operate the exemplary device without any physical connections to the exterior of the body; or, if using an external laser source, with the only physical connection to the exterior of the body being for the delivery of the laser light.

Figure 2:
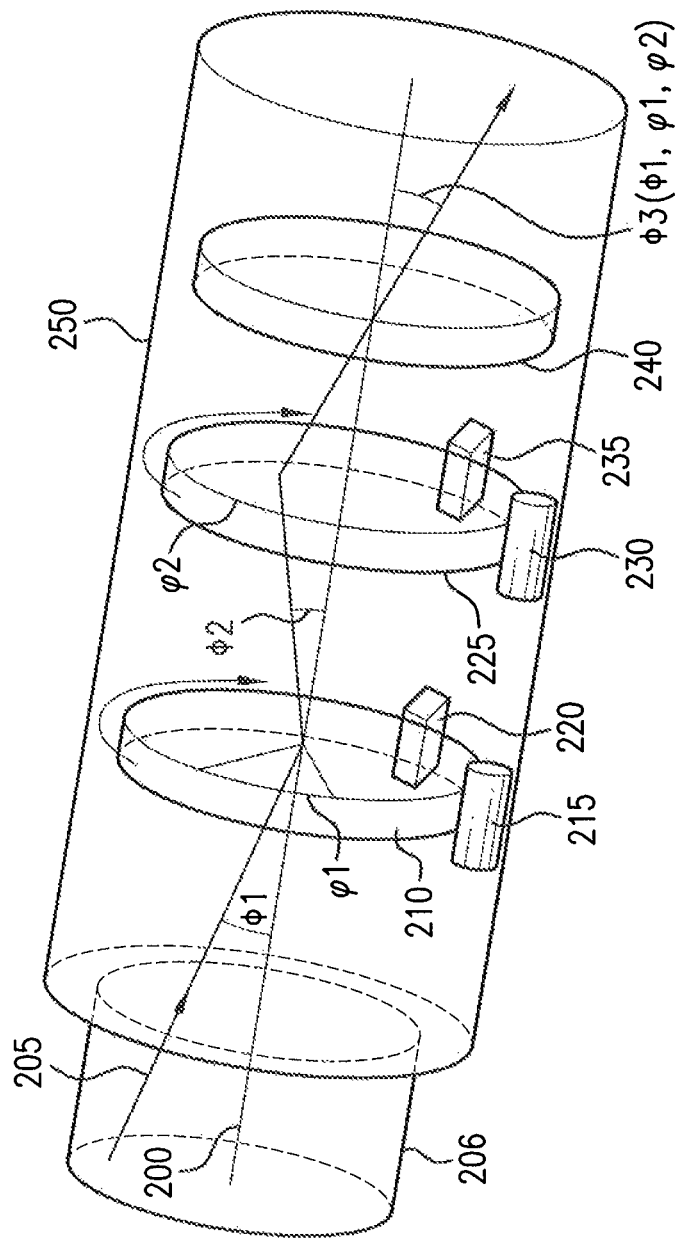
FIG. 2 is a perspective view of a laser scanning endoscopic head of the exemplary laser scalpel system of FIG. 1 in accordance with a first exemplary embodiment of the present disclosure.

FIG. 2 shows a perspective view of a laser scanning endoscopic head of the exemplary laser scalpel system of FIG. 1 in accordance with a first exemplary embodiment of the present disclosure. For example, the laser scanning endoscopic head shown in FIG. 2 can have one or more exemplary transmissive elements 210 and 225 (e.g., refractive and/or diffractive elements), aligned with their centers on an optical axis 200. At least one light beam 205 can be delivered by a light delivery mechanism/arrangement 206 incident on the first element 210 at a first angle φ1 with respect to the optical axis 200. As illustrated in FIG. 2, the light beam 205 can be refracted or diffracted by the exemplary first element 210, and emerge at a different second angle φ2 with respect to the optical axis 200. The light beam 205 can also emerge from the first element 210 with a rotation angle and/or azimuthal angle around the optical axis that is dependent on the rotation angle φ1 of the first element 210 around the optical axis 200. The rotation angle φ1 can be actuated on and/or controlled by a motor 215 and an angular position sensor 220 in a servo control positioning arrangement, for example. The exemplary motor 215 can be provided in the endoscopic head, or adjacent thereto, according to one exemplary embodiment.

As further illustrated in FIG. 2, the exemplary second element 225 can receive the light at the first angle φ2 with respect to the optical axis 200, and can induce a further refraction or diffraction of the light beam 205 such that the resultant light beam 205 emerges at a third angle φ3 with respect to the optical axis, and with a rotation and/or azimuthal angle around the optical axis 200. According to this exemplary arrangement, the rotation angle φ1 around the optical axis 200 at which the light beam 205 emerges from the second element 225 is dependent on another rotation angle φ2 of the second device 225 which can be actuated and/or controlled by a second motor 230 and a second angular position sensor 235, operated in a servo control positioning configuration, for example. Thus, the angle of the light emerging from the second element 225 can have the following dependencies: φ3 (φ1, φ1, φ2) according to the exemplary arrangement illustrated in FIG. 2.

Additionally, an exemplary focusing element 240 can be included in the exemplary system shown in FIG. 2. In particular, the exemplary arrangement illustrated in FIG. 2 can be configured so that focusing element 240 follows the two elements 210, 225 to focus the light beam 205 onto the target tissue in the body cavity, for example. The components illustrated in FIG. 2 and described herein can be housed or situated in a structure and/or housing 250 which can be configured, sized and/or structured to be inserted into a body cavity of a person, animal or any other creature for which the exemplary device in accordance with the present disclosure can be utilized.

FIG. 3A shows a functional illustration of a laser scanning endoscopic head of the exemplary laser scalpel system of FIG. 1 in accordance with a first exemplary embodiment of the present disclosure. Exemplary optical elements 300, 310 can each be optical wedges or prisms, or diffraction gratings, or any combination and/or hybrid thereof, for example. According to certain exemplary embodiments of the laser scanning endoscopic head, the optical elements 210, 225 illustrated in FIG. 2 can be the same as or substantially similar to optical elements 300 and 310 illustrated in FIG. 3.

FIG. 3B shows an illustration of an exemplary scanning pattern 320 generated using the exemplary optical elements of FIG. 3A. As illustrated in FIG. 3B, the scanning pattern 320 (e.g., a scanned area) can be defined by the light beam 205 emerging from the second element 225, and thus is dependent on the rotation angles φ1, φ2 of the optical elements 210, 225, respectively.

Figures 4A, 4B:
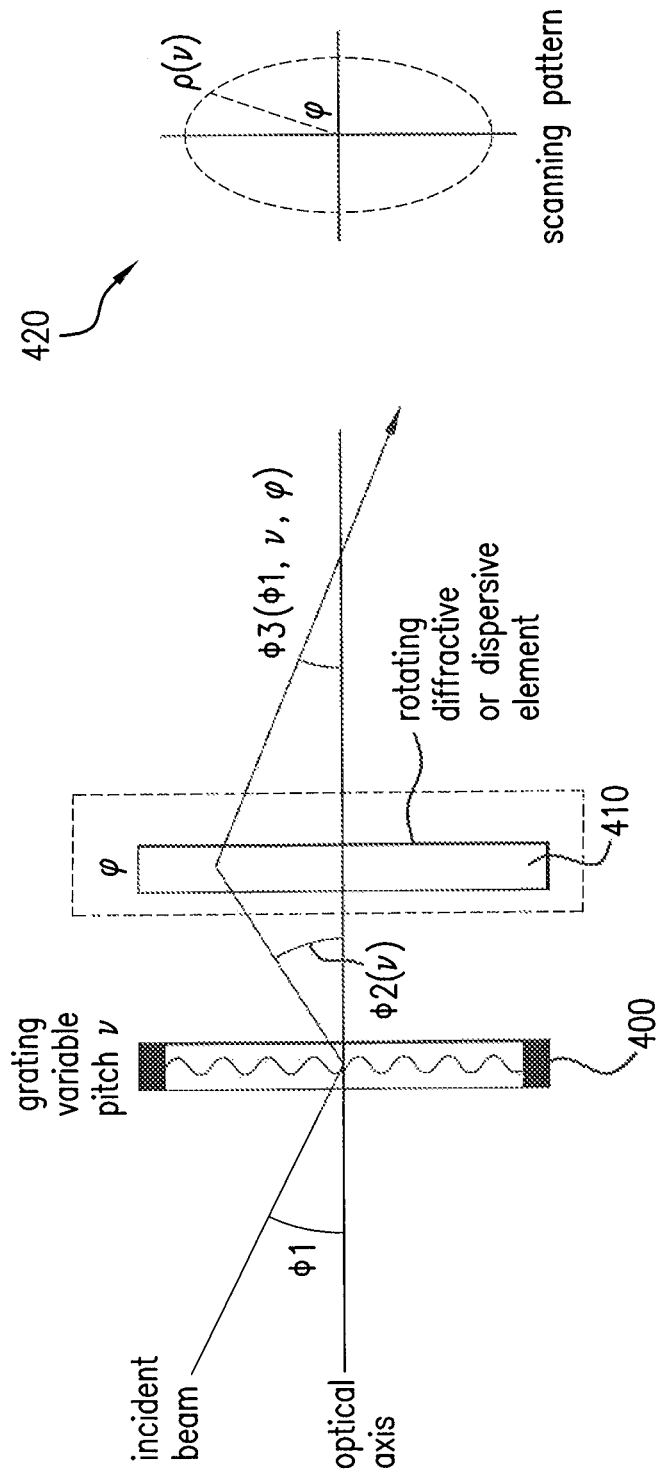
FIG. 4A is a sketch of optical elements that can be included in the laser scanning endoscopic head according to a second exemplary embodiment of the present disclosure.
FIG. 4B is an illustration of an exemplary scanning geometry generated by the exemplary optical elements of FIG. 4A.

FIG. 4A shows a side view of further optical elements that can be included in the laser scanning endoscopic head according to a second exemplary embodiment of the present disclosure. The exemplary optical elements 400, 410 illustrated in FIG. 4A can be used in an exemplary device having the same or similar basic configuration as the exemplary laser scanning endoscopic head shown in FIG. 2. However, according to the exemplary embodiment of the device illustrated in FIG. 4A, the first optical element 400 can be a fixed (e.g., non-rotating) grating with a variable pitch. For example, a first optical element 400 can be an acousto-optical device or a liquid crystal device. The optical element 400 can modify the second angle φ2 of the diffracted light beam by varying the grating pitch v. As also illustrated in FIG. 4A, the second optical element 410 can be an optical wedge or prism, or diffraction grating that can rotate about the optical axis to induce the refraction and/or the diffraction of the diffracted light beam. Exemplary optical elements 400,410 can be aligned with their centers on the optical axis.

FIG. 4B shows an illustration of an exemplary scanning pattern 420 generated by the exemplary optical elements 400, 410 of FIG. 4A. As illustrated in FIG. 4B, the resulting scanning pattern 420 can be an ellipse with the long axis orthogonal to the ruling of the fixed grating of the first optical element 400.

Figure 5B:
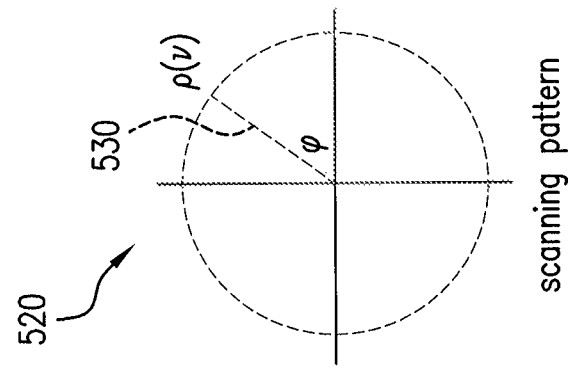
FIG. 5B is an illustration of an exemplary scanning geometry generated by the exemplary optical element of FIG. 5A.
Figure 5A:
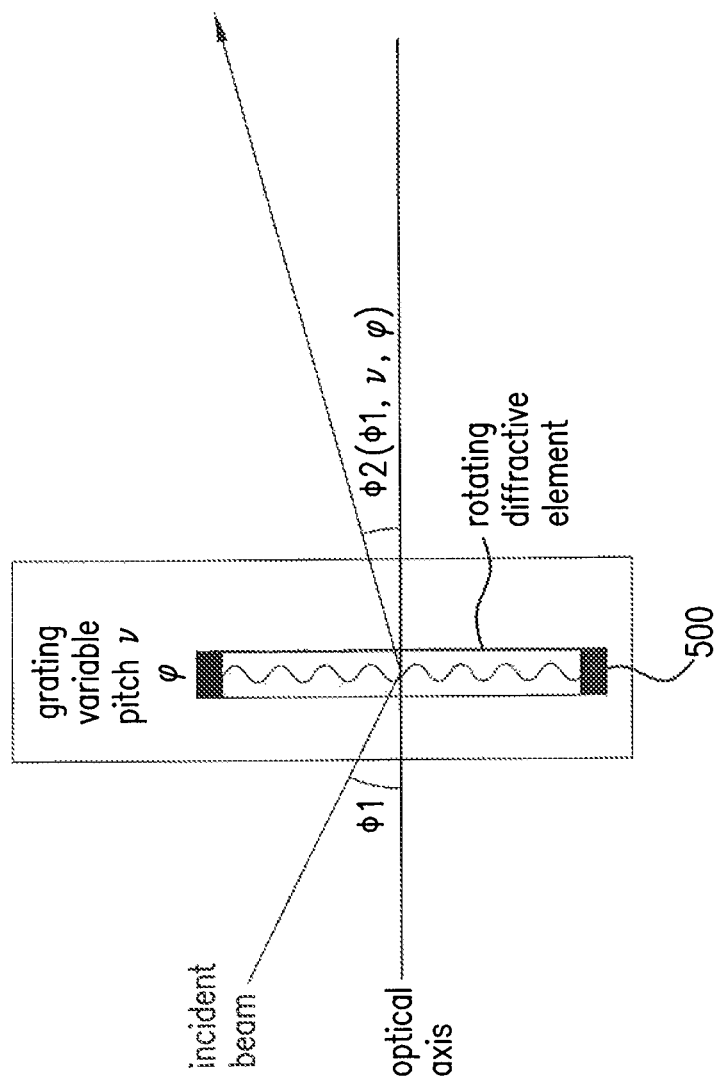
FIG. 5A is a sketch of a particular optical element that can be included in the laser scanning endoscopic head according to a third exemplary embodiment of the present disclosure.

FIG. 5A shows a side view of a particular optical layout that can be included in the laser scanning endoscopic head according to a third exemplary embodiment of the present disclosure. Based on a basic configuration similar or that of the exemplary laser scanning endoscopic head illustrated in FIG. 2, an exemplary device in accordance with the present disclosure can have a single optical element 500, as illustrated in FIG. 5A. For example, the optical element 500 can be a single rotating diffraction grating of variable pitch, such as an acousto-optical device or a liquid crystal device. The diffracted angle (or elevation angle) φ2 can be varied by modifying the pitch of the grating v. The angle around the optical axis (or azimuthal angle) can be varied by rotating the optical element 500 by an angle φ.

FIG. 5B an illustration of an exemplary scanning pattern 520 generated by the exemplary optical element 500 of FIG. 5A. As illustrated in FIG. 5B, the scanning pattern 520 resulting from the exemplary embodiment of a device according to the present disclosure illustrated in FIG. 5A can be a circle. The radius of the circle 530 can be dependent on the grating pitch of the optical element 500.

Figure 6B:
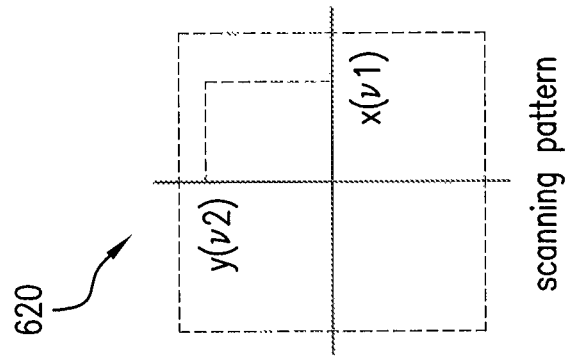
FIG. 6B is an illustration of an exemplary scanning geometry generated by the exemplary optical elements of FIG. 6A.
Figure 6A:
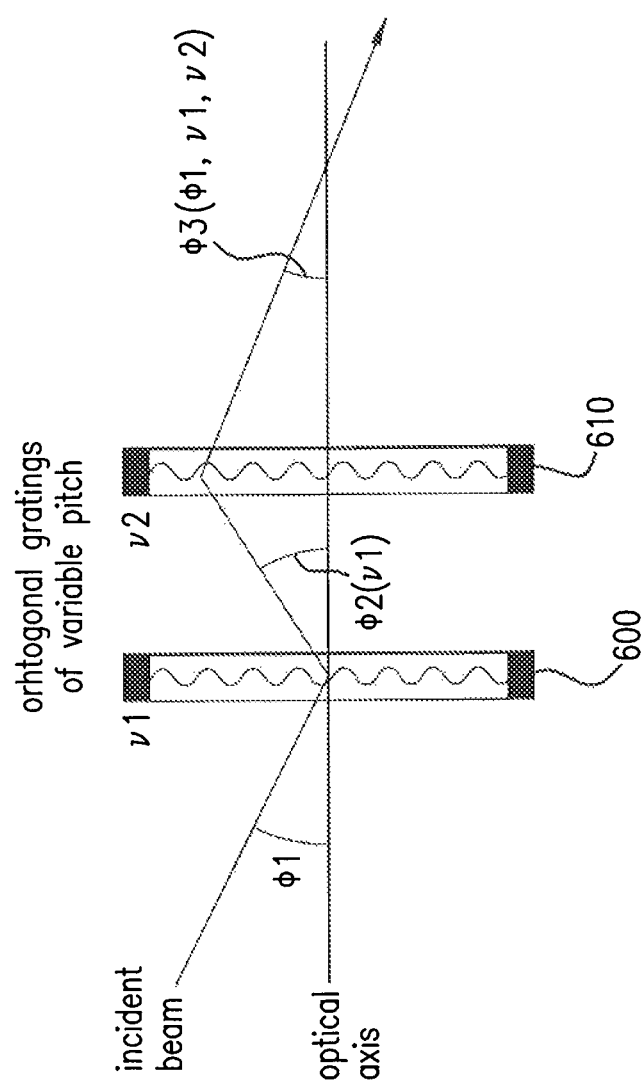
FIG. 6A is a sketch of still other optical elements that can be included in the laser scanning endoscopic head according to a fourth exemplary embodiment of the present disclosure.

FIG. 6A shows a side view of still another optical element arrangement that can be included in the laser scanning endoscopic head according to a fourth exemplary embodiment of the present disclosure. The exemplary optical elements 600, 610 illustrated in FIG. 6A can also be used in an exemplary device having the same or similar basic configuration as that of the exemplary laser scanning endoscopic head illustrated in FIG. 2. However, according to the exemplary embodiment of the device shown in FIG. 6A, the optical elements 600, 610 can both be fixed (e.g., non-rotating) and orthogonal diffraction gratings of variable pitch v1 and v2, respectively, such as acousto-optical devices or liquid crystal devices. As illustrated in FIG. 6A, the diffracted angle φ3 of the light beam emerging from optical element 610 can be dependent on the incident angle φ1 of the light beam and the grating pitches v1 and v2 of the optical elements 600 and 610, respectively. Thus, for example, in accordance with certain exemplary embodiments of the present disclosure, it is possible to modify the position of the delivery of the refracted and/or diffracted light to the target location in the body by modifying and/or controlling the pitch of the grating(s) without using any actuators, motors and/or sensors to modify and/or control the position and/or orientation of the optical element(s).

FIG. 6B shows an illustration of an exemplary scanning pattern 620 generated by the exemplary optical elements 600, 610 of FIG. 6A. As illustrated in FIG. 6B, the resulting scanning pattern 620 of this embodiment is a rectangle with Cartesian coordinates dependent on the pitches v1 and v2 of the two gratings of optical elements 600 and 610, respectively.

Further, in accordance with certain exemplary embodiments of the present disclosure, it is possible to modify the position of the delivery of the refracted and/or diffracted light to the target location in the body by modifying and/or controlling at least one characteristic of the incident light beam, such as the frequency and/or wavelength of the light, e.g., without using any actuators, motors and/or sensors to modify and/or control the position and/or orientation of the optical element(s).

Figures 7A, 7B:
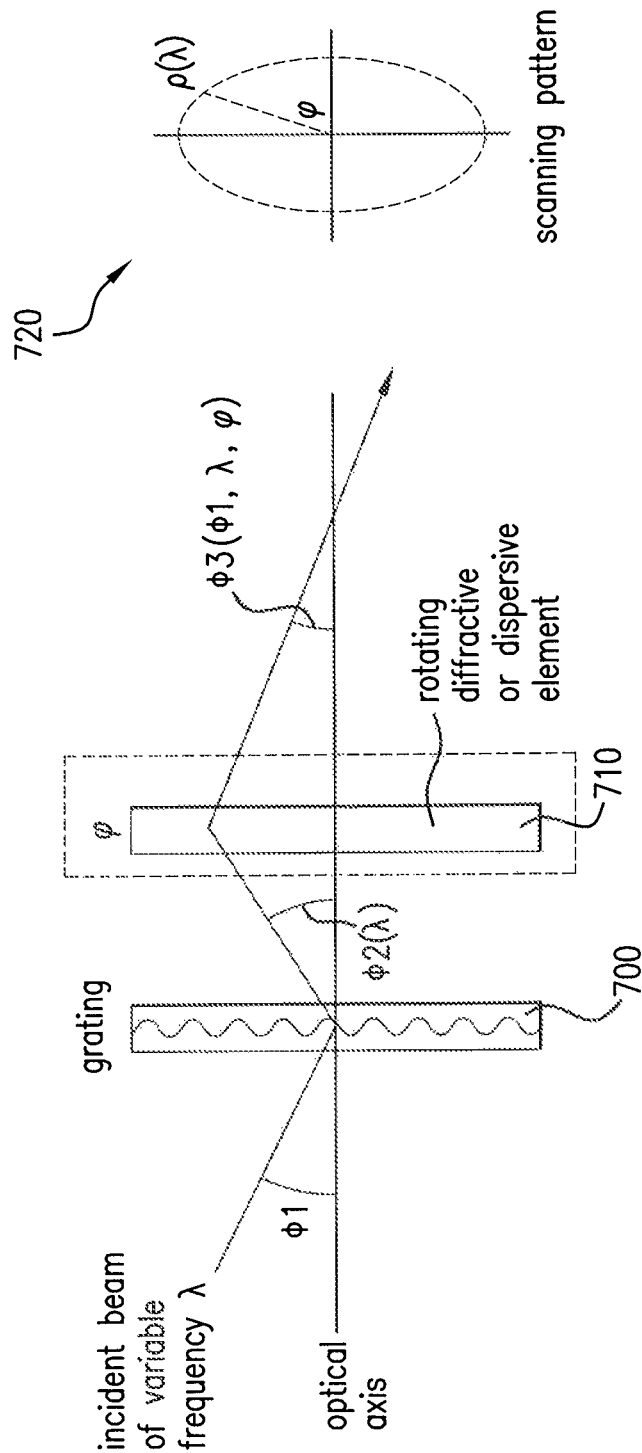
FIG. 7A is an illustration of further optical elements that can be included in the laser scanning endoscopic head according to a fifth exemplary embodiment of the present disclosure.
FIG. 7B is an illustration of an exemplary scanning geometry generated by the exemplary optical elements of FIG. 7A.

FIG. 7A shows a side view of a further optical arrangement that can be included in the laser scanning endoscopic head according to a fifth exemplary embodiment of the present disclosure. The exemplary optical elements 700, 710 illustrated in FIG. 7A can be used in an exemplary device having the same or similar basic configuration as that of the exemplary laser scanning endoscopic head illustrated in FIG. 2. Similarly to the configuration illustrated in FIG. 4A, the first optical element 700 can be a fixed (e.g., non-rotating) grating with a variable pitch, and the second optical element 710 can be an optical wedge or prism, or a diffraction grating of fixed pitch. Similarly to the configuration illustrated in FIG. 4A, the second optical element 710 can rotate with respect to the optical axis to induce a refraction or diffraction of the diffracted beam. Unlike the exemplary configuration illustrated in FIG. 4A, however, according to the exemplary embodiment illustrated in FIG. 7A, the second angle $\phi 2$ (elevation angle) of the diffracted light beam can be varied by modifying the frequency and/or wavelength of the incident light beam.

FIG. 7B shows an illustration of still further exemplary scanning pattern 720 generated by the exemplary optical elements 700, 710 of FIG. 7A. As illustrated in FIG. 7B, the resulting scanning pattern 720 of the exemplary embodiment of a device according to the present disclosure illustrated in FIG. 7A can be an ellipse, with the long axis being orthogonal to the grating direction, for example.

Figure 8B:
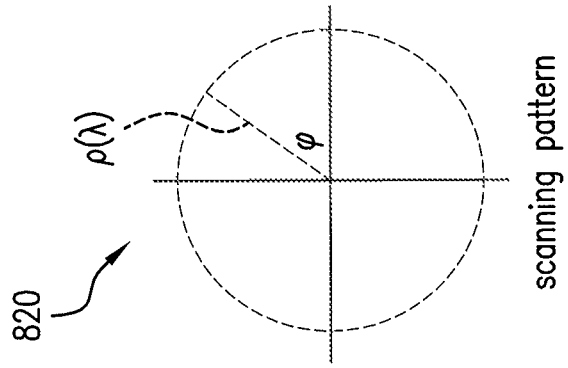
FIG. 8B is an illustration of an exemplary scanning geometry generated the exemplary optical element of FIG. 8A.
Figure 8A:
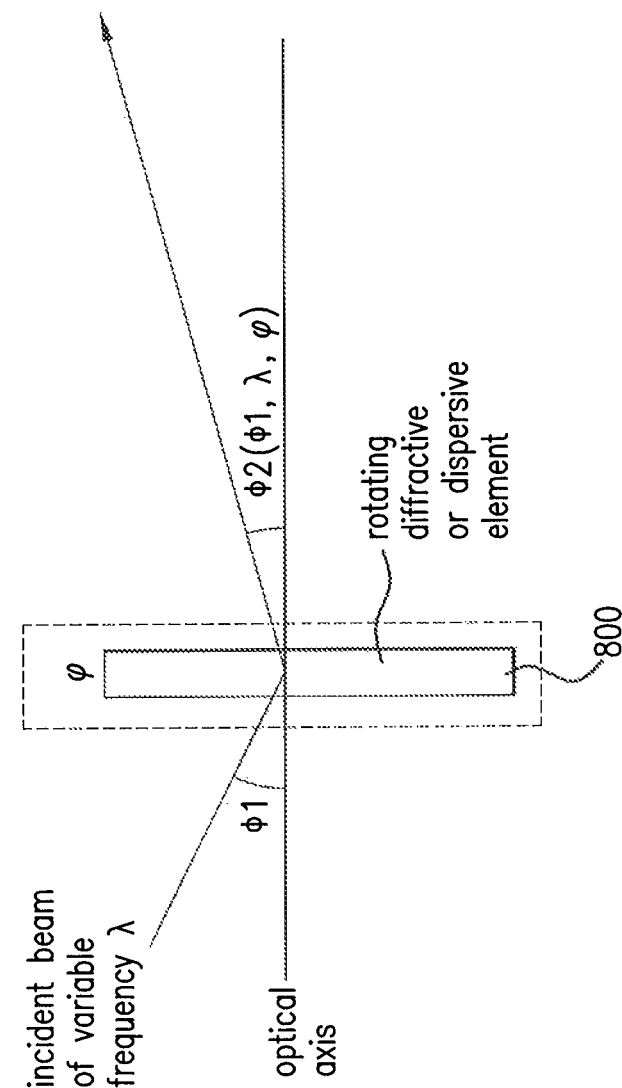
FIG. 8A is an illustration of yet another optical configuration that can be included in the laser scanning endoscopic head according to a sixth exemplary embodiment of the present disclosure.

FIG. 8A shows a side view of yet another optical arrangement that can be included in the laser scanning endoscopic head according to a sixth exemplary embodiment of the present disclosure. The exemplary embodiment of a device according to the present disclosure illustrated in FIG. 8A has a similar configuration as the exemplary embodiment of the exemplary device illustrated in FIG. 7A, with an incident light beam of variable frequency/wavelength. Unlike the exemplary configuration illustrated in FIG. 7A, however, the exemplary configuration illustrated in FIG. 8A has a single optical element 800, which can be an optical wedge or prism, or a diffraction grating of fixed pitch that can rotate about the optical axis to induce a rotation azumuthal angle of the diffracted light beam.

FIG. 8B is an illustration of an exemplary scanning pattern 820 generated the exemplary optical element 800 of FIG. 8A. As illustrated in FIG. 8B, the resulting scanning pattern 820 of the exemplary embodiment of a device according to the present disclosure illustrated in FIG. 8A can be circular.

Figure 9A:
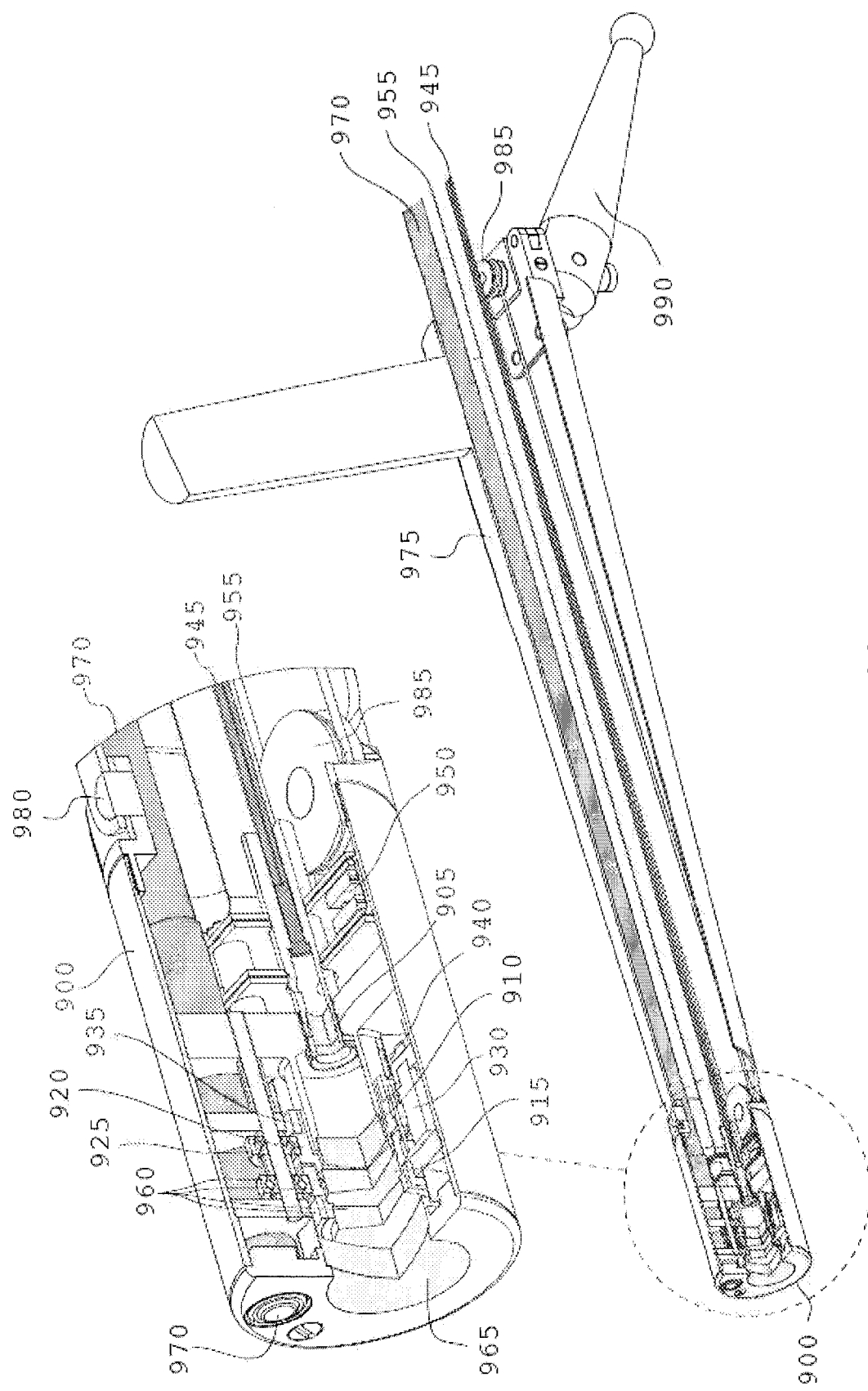
FIG. 9A are illustrations of an endoscopic laser scalpel device and a cutout view at a head section thereof, in accordance with an exemplary embodiment of the present disclosure.

FIG. 9A shows illustrations of an endoscopic laser scalpel device and a cutout view at a head section thereof, in accordance with an exemplary embodiment of the present disclosure. As illustrated in FIG. 9, the exemplary device includes a hollow core optical fiber 945 that can deliver the $CO_2$ infrared laser light to the endoscopic scanning head 900. The exemplary device can be configured such that the laser and/or light can first be expanded with a negative lens 905 and then collimated by a positive lens 910 to fill the aperture of scanning optical prisms or wedges 915, 960. The first scanning optical prism or wedge 915 can be mounted on a rigid ring (or ring mount) 920 that may be held in place by an array of bearings 925. Ring 920 can be rotated by an ultrasonic motor 930, for example. A magnetic ring 935 can be attached to the rigid ring 920, and the position of the magnetic ring 935 can be measured and/or monitored, such as by a hall sensor array 940. An ultrasonic motor 930 and the hall position sensor 940 can be controlled in a servo loop arrangement by, e.g., a local processor 950 in response to movement commands that can be delivered from a scanner control unit, such as the scanner control unit 135 illustrated in FIG. 1. The movement commands can be delivered via a signal bus 955 or a wide variety of other wired and/or wireless communication systems and protocols.

As further illustrated in FIG. 9A, a second wedge or prism electro-opto-mechanical unit/arrangement 960 can follow (e.g., be located further away from the light source than) the first mechanical unit, and may include a second prism, mounting ring, bearing array, ring magnet, and hall position sensor. The second mechanical unit/arrangement 960 can also be under servo control by the local processor 950. A focusing positive lens 965 can interface the endoscopic head to the body cavity, and can define the working distance, field of operation and resolution of the endoscopic scanning head.

According to the exemplary embodiment of the endoscopic laser scalpel system, device, apparatus and arrangement shown in FIG. 9A, some or all of the scanner optics can be composed of zinc selenide (ZnSe) and configured for use with $CO_2$ laser light. While one having ordinary skill in the art can understand in view of the teachings herein that other materials can be used, the use of ZnSe can be preferred because of its relatively low bulk absorption coefficient and good antireflection properties, in comparison to other materials that can be used.

The endoscopic head can include a fiberscope 970 and/or other endoscopic imaging device adjacent to, and with a fixed relation to, the scanner. The fiberscope 970 can be configured to provide or facilitate the illumination to the tissue sample in the body cavity, as well as relay a live video image to the external video processor and image display, such as the video processor 115 and the display 120 illustrated in FIG. 1, for example. Data and/or information associated with the video image can also be stored in a storage arrangement and/or storage device, which can include a hardware non-transitory computer-accessible medium for subsequent display and/or processing, for example.

According to certain exemplary embodiments of the system, device, apparatus and arrangement of the present disclosure, one or more additional channels configured to be parallel (or substantially parallel) to the fiberscope 970 can be provided in the endoscopic head. Such additional channel(s) can vary in size and/or cross-sectional shape, and may be configured and used to provide delivery and/or removal of liquids, gasses and/or small solids from the body cavity, for example. For example, the additional channel(s) can also be configured and/or used for insertion and removal of other surgical instruments, devices, tools, detectors and/or sensors, etc.

According to the exemplary embodiment of the system, device, apparatus and arrangement illustrated in FIG. 9A, the endoscopic head can be mounted at the end of a Kleinstasser or Steiner operating laryngoscope 975 with a moveable coupling 980 that can provide a panning motion of the endoscopic scanning head through a pulley system 985 and an external manipulating lever lock 990. It is also possible to mount the endoscopic scanning head on a flexible endoscope, such as a gastroendoscope or a sigmoidoscope. As an alternative to using a fiberscope (or in conjunction therewith), an imaging sensor, such as a CCD or CMOS imaging chip, can be incorporated into the exemplary scanning head to provide the live image of the tissue, for example. A separate illumination path also can be provided in the exemplary scanning head 900.

Further, according to another exemplary embodiment of the present disclosure it is possible to incorporate two or more imaging devices (e.g., detector chips, imaging devices, and/or fiberscopes) in the exemplary scanning head to produce a stereoscopic image of the tissue in the body cavity that can be used to provide greater control of the device to the user (e.g., operating surgeon). According to such exemplary embodiments, the front focusing lens can be adjusted to modify the working distance, field of operation, and laser spot size of the scanning head, for example. It is also possible using certain exemplary embodiments of the system, device, apparatus and arrangement according to the present disclosure to be configured or structured for positioning the scanning head 900 remotely through an electromechanical arrangement so as to provide for the use of such exemplary embodiments of the system, device, apparatus and arrangement in telemedicine, for example. Communication interfaces can be used to facilitate real-time direct communication and/or communication via the Internet, for example, so as to facilitate a user located off-site to remotely control and/or use the exemplary system, device, apparatus and arrangement. The implementation of simulations and/or pre-programmed procedures can also be used to overcome any time-delays that can result from the user being located off-site and otherwise pose a possible difficulty in the performance of certain time-critical operations. It also is possible to incorporate or include an accelerometer and/or a stabilization system in the scanner head to compensate for any unwanted movement during operation, for example.

Figure 9B:
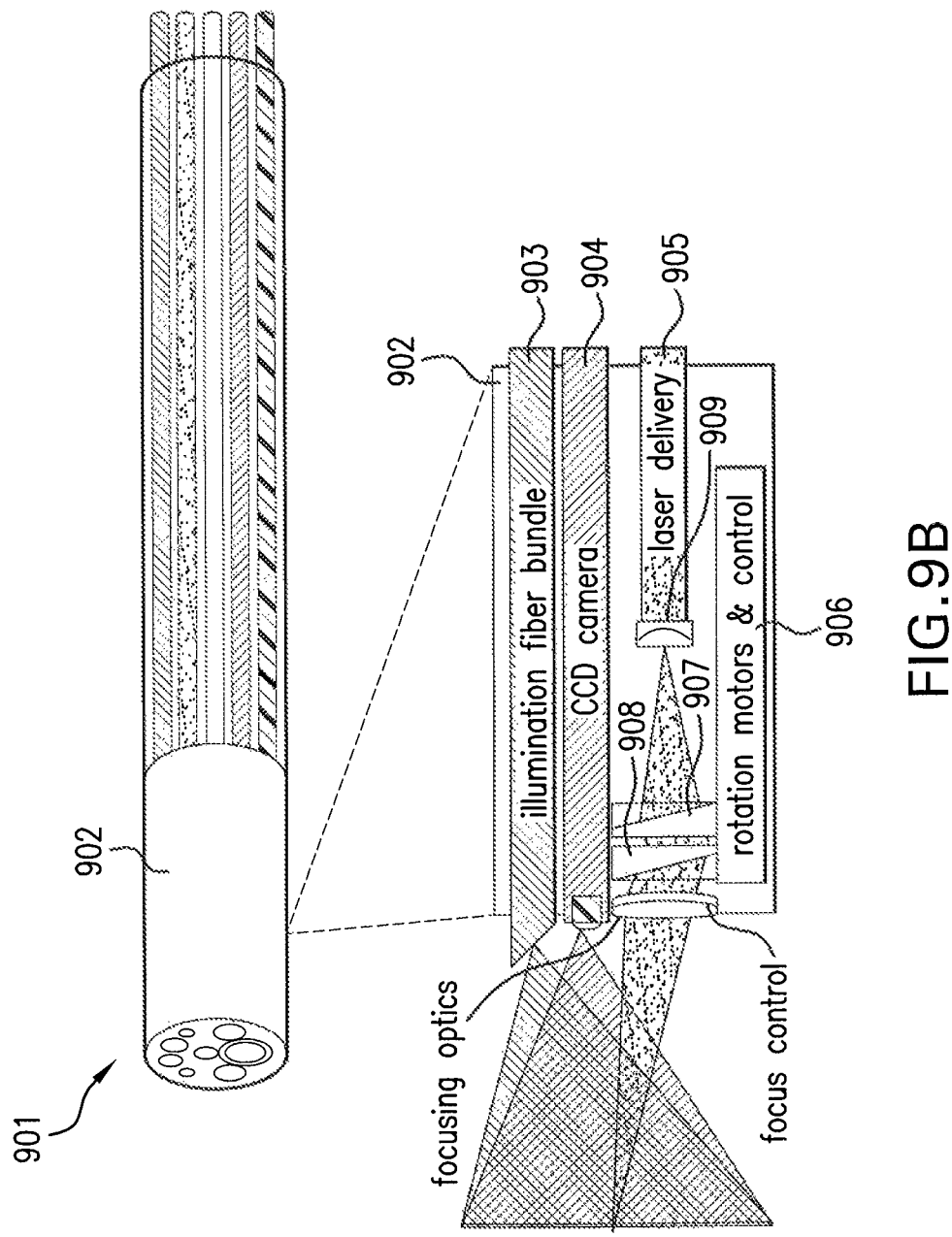
FIG. 9B are illustrations of the endoscopic laser scalpel device and a cutout view of at the head section thereof, in accordance with another exemplary embodiment of the present disclosure.

FIG. 9B shows illustrations of the endoscopic laser scalpel device 901 and a cutout view of at the head section 902 thereof, in accordance with another exemplary embodiment of the present disclosure. A hollow-core fiber for $CO_2$ laser delivery can be used for the endoscopic laser scalpel device 901 according to certain exemplary embodiments of the present disclosure. It is also possible to include and/or utilize other elements/components/arrangements in addition to the scanning optics, and such other elements/components/arrangements can be located, e.g., adjacent to the scanning optics. For example, these other elements/components/arrangements can include, e.g., (a) an illumination channel 903 (e.g., optical fiber or LED), (b) a video channel 904 (e.g., which can include CCD and/or fiber bundle), (c) a laser delivery channel 905 (e.g., single or multimode optical fiber, articulated arm delivery configuration or line-of-sight delivery configuration), (d) an electromechanical control channel 906 that can be used for two or more separate and independent optical scanning elements 907, 908, (e) other co-axial optical beam shaping and focusing elements 909 (e.g., focusing and/or correction optics), (f) a remote control system that can be used for positioning and/or orientating the endoscope head (e.g., which can include angulation control wires and pulleys), and (g) additional channels, working ducts and/or instruments that can be used for, e.g., delivery and/or removal of fluids, gasses, small solids and/or other instruments, devices and tools.

As shown in FIG. 9B, the rotation and control of the optical elements 907, 908 (e.g., optical wedges and/or prisms) can be located or provided in the endoscope head 902 according to certain exemplary embodiments of the present disclosure, and configured/structured to perform certain exemplary methods and procedures in accordance with further exemplary embodiments of the present disclosure for miniaturization and precision, for example. This can be achieved, e.g., using micro-motors and/or actuators located in the endoscope head 902 that can be controlled remotely. Because optical elements 907, 908 may have little mass or weight, it is possible to use small actuators in the endoscopic head 902, and maintain accuracy and speed of the exemplary device, system, apparatus and/or arrangement according to the exemplary embodiment of the present disclosure. For example, an exemplary mechanical system can be used to control simple and complex movements and/or rotations of the wedges 907, 908, including, e.g., accelerations, reversals and repetitions, in response to a user's (e.g., surgeon's) interaction with a video image and the pointing device. Exemplary imaging and illumination channels can be provided to facilitate a retrieval and generation of an endoscopic image of, e.g., 200 lines (or better) of the field in front of the endoscope head to a depth of approximately 2 cm-10 cm, for example. The mathematical relationship between the Cartesian space of an image screen and the dual-angle space of exemplary optical elements which should be understood by those having ordinary skill in the art can facilitate exemplary results.

Additionally, according to certain exemplary embodiments of the present disclosure, a light detector and/or analyzer can be incorporated in the scanner head. Information and/or data can be obtained from the light detector and displayed in real-time, processed and/or stored in a storage arrangement and/or storage device, and used in real-time or subsequently to analyze the scattered light from the surgical laser and/or the light reflected from the tissue. Such exemplary data, information and/or analysis can be used to assess and/or review the performance of the laser device, system, method, arrangement and/or apparatus and effects of the laser surgery, for example.

While certain types of optical elements have been described herein, one having ordinary skill in the art should appreciate in view of the teachings of the present disclosure that relatively lower-cost Germanium optics in the scanner can be used in accordance with certain exemplary embodiments of the present disclosure. It is also possible to use a combination of a laser control and various different optics. For example, Table 1 shows exemplary numerical data and parameters for exemplary combinations of laser control and different optics in accordance with certain exemplary embodiments of with the present disclosure. One having ordinary skill in the art should appreciate, based on the teachings of the present disclosure, that other exemplary combinations of laser control and different optics can be used in accordance with certain exemplary embodiments of the present disclosure.

TABLE 1

Exemplary numerical data and parameters for exemplary combinations of laser control and different optics in accordance with the present disclosure

| # | Type | Comment | Curvature | Thickness | Glass | Semi-Diameter | Parameter 1 | Parameter 2 |
|---|------|---------|-----------|-----------|-------|---------------|-------------|-------------|
| 0.0000 | STANDARD | | 0.0000 | inf | | 0.0000 | 0.0000 | 0.0000 |
| 1.0000 | PARAXIAL | | 0.0000 | 75.0000 | | 0.1500 | −5.0000 | 1.0000 |
| 2.0000 | TILTSURF | WEDGE | 0.0000 | 2.7200 | ZNSE | 6.3500 | −0.0524 | 0.0000 |
| 3.0000 | STANDARD | | 0.0000 | 0.5000 | | 6.3500 | 0.0000 | 0.0000 |
| 4.0000 | STANDARD | wedge | 0.0000 | 2.7200 | ZNSE | 6.3500 | 0.0000 | 0.0000 |
| 5.0000 | TILTSURF | | 0.0000 | 1.0000 | | 6.3500 | 0.0524 | 0.0000 |
| 6.0000 | STANDARD | laser rsrch opt | 0.0000 | 1.6000 | ZNSE | 7.6200 | 0.0000 | 0.0000 |
| 7.0000 | STANDARD | LX-0620-Z-ET1 .5 | −0.0140 | 0.0000 | | 7.6200 | 0.0000 | 0.0000 |
| 8.0000 | STANDARD | | 0.0000 | 128.4603 | | 2.5718 | 0.0000 | 0.0000 |
| 9.0000 | STANDARD | | 0.0000 | 0.0000 | | 18.4306 | 0.0000 | 0.0000 |

Figure 10:
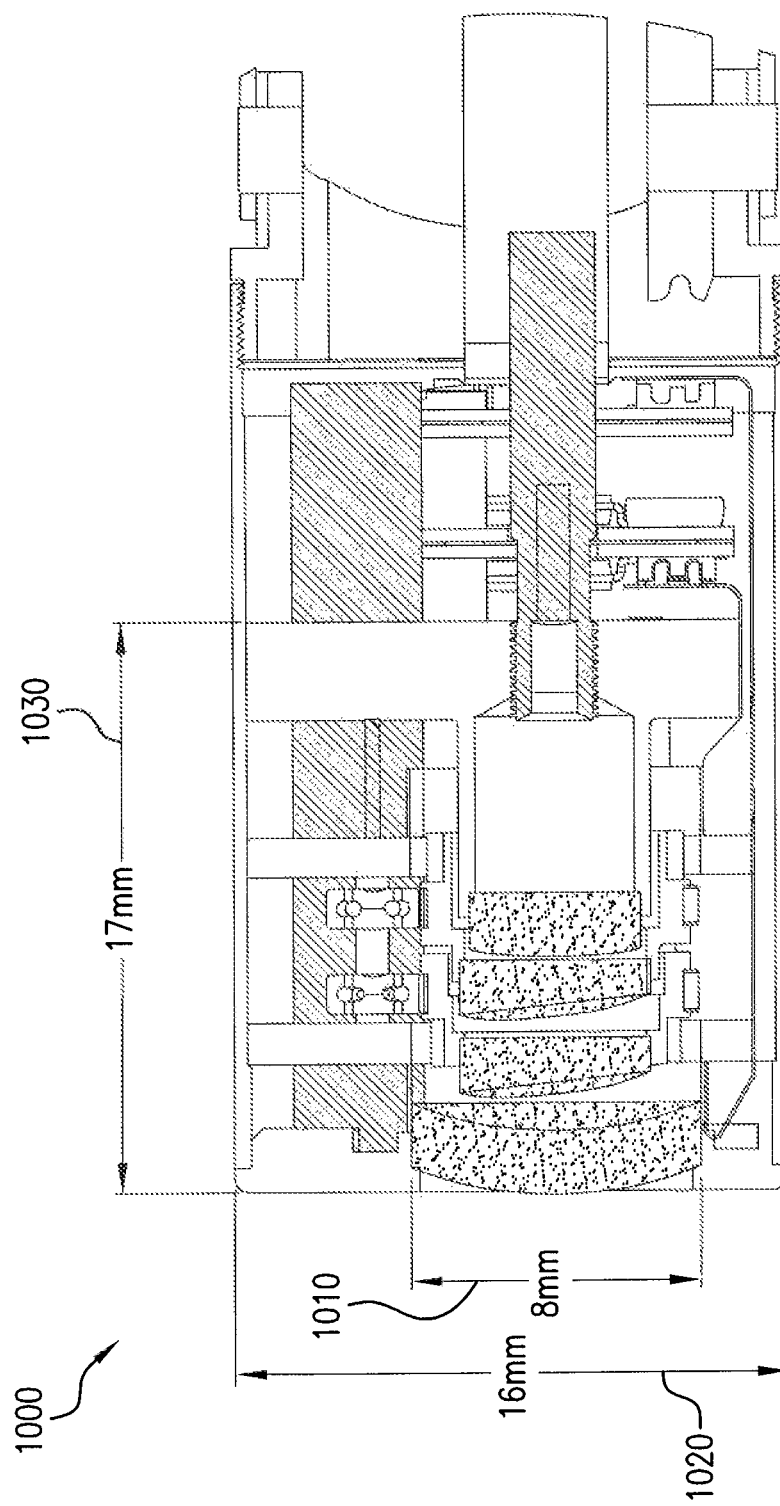
FIG. 10 is a side cross-sectional view of a laser scanning endoscopic head along with representative dimensions thereof in accordance with an exemplary embodiment of the present disclosure.

FIG. 10 shows a side cross-sectional view of a laser scanning endoscopic head 1000 along with representative dimensions thereof in accordance with an exemplary embodiment of the present disclosure, in which the diameter of the scanner optics can define the numerical aperture of the surgical laser beam. For example, as illustrated in FIG. 10, a diameter of the scanner optics 1010 according to an exemplary embodiment of the present disclosure can be approximately 8 mm. It is also possible for the diameter of the scanner optics 1010 to be in the range of approximately 2 mm to 14 mm. Other exemplary ranges for the diameter of the scanner optics 1010 can be 4 mm to 12 mm, 6 mm to 10 mm (or approximations thereof), etc. It should be understood that the diameter of the scanner optics 1010 can be smaller than 2 mm or larger than 15 mm in accordance with certain exemplary embodiments of the present disclosure. With the diameter of the scanner optics 1010 being approximately 8 mm, an aperture diameter can be approximately 5 mm, for example.

As further illustrated in FIG. 10, the diameter 1020 of the head 1000 can be dependent on other elements and/or components in the exemplary system in addition to the optics, such as, e.g., imaging, illumination and instrument channels, motors, processors, controls systems, etc. For example, the diameter 1020 of the head 1000 can be approximately 16 mm, as illustrated in FIG. 10. It is also possible for the diameter 1020 of the head 1000 to be in a range of approximately 8 mm to 24 mm. For example; the diameter 1020 of the head 1000 can also be 10 mm to 22 mm, 12 mm to 20 mm (or approximations thereof), etc. It should be understood that the diameter 1020 of the head 1000 can be smaller than 8 mm or larger than 24 mm in accordance with certain exemplary embodiments of the present disclosure. The diameter 1020 of the head 1000 can depend on several factors, including the application(s) for which the system is to be used, the features (e.g., channels) to be included in the head, and the associated manufacturing feasibility and expense, for example. Accordingly, considering precision manufacturing and technologies related to producing the optics and other elements that can be included in an exemplary system and device according to the present disclosure, it may be possible to produce heads having continuously smaller diameters will be possible and is thus considered to be in accordance with the present disclosure.

The length of the head 1000 can depend on the optical design, the selection, and/or the configuration of the optical elements used to generate the scan. For example, a length 1030 of the head 1000 can be approximately 17 mm, as illustrated in FIG. 10. It is also possible for the length 1030 of the head 1000 to be in a range of approximately 9 mm to 25 mm. Further, the length 1030 of the head 1000 can be 11 mm to 23 mm, 13 mm to 21 mm (or approximations thereof), etc. For example, the length 1030 can be smaller than 9 mm or larger than 25 mm in accordance with certain exemplary embodiments of the present disclosure.

Figure 11:
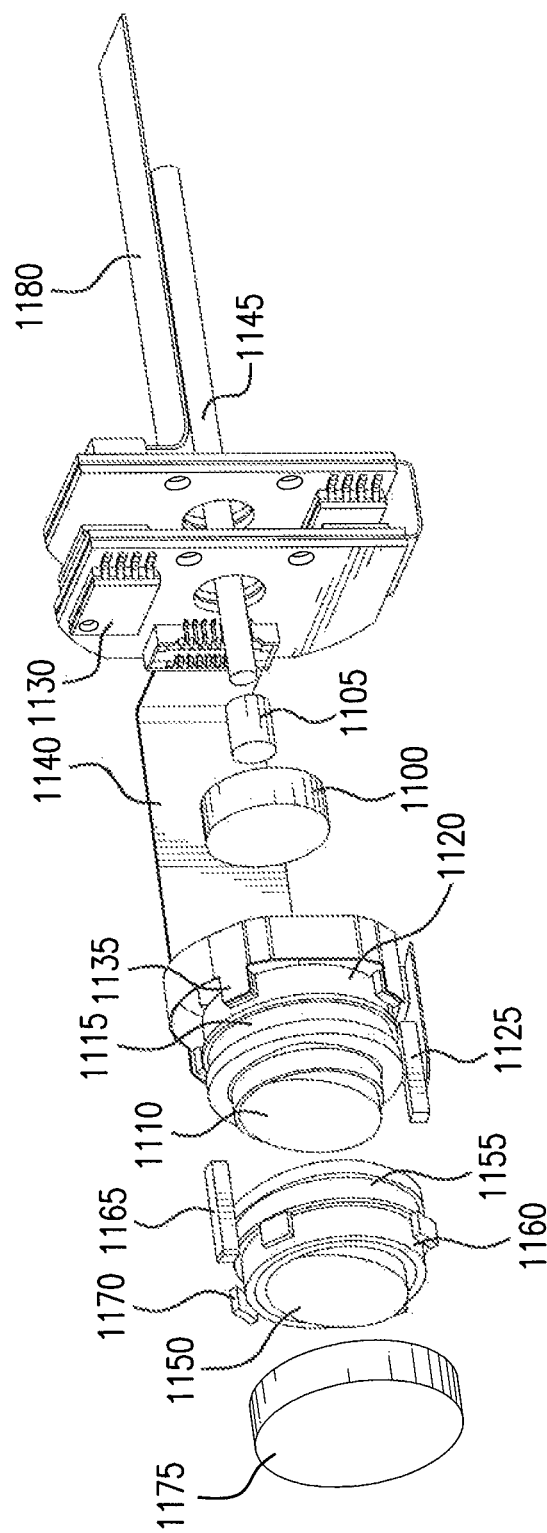
FIG. 11 is a perspective view of a servo controlled positioning system in accordance with an exemplary embodiment of the present disclosure.

FIG. 11 shows a perspective view of a servo controlled positioning system in accordance with an exemplary embodiment of the present disclosure. The exemplary scanner illustrated in FIG. 11 can include one or more optical fibers 1145 that can be configured to deliver the light to the exemplary system, device, apparatus, arrangement, etc. Two or more lenses 1100, 1105 can expand and/or collimate the light beam to fill the aperture of the scanner elements. A first scanning wedge 1110 can be mounted on a mounting ring 1115 with a magnetic ring 1120 fixed concentrically with respect thereto. An ultrasonic motor 1125 can be configured to rotate the mounting ring 1115 with the direction and acceleration being controlled by a microprocessor/frequency generator arrangement 1130. An array of four or more orthogonal magnetic detectors 1135 can relay (and/or communicate) the rotational position of the magnetic ring to the arrangement 1130. The ultrasonic motor 1125 and the detector(s) 1135 can be connected to the arrangement 1130 through a signal bus 1140 in a servo control arrangement, for example. It is also possible to use other communication system(s), configuration(s) and/or protocol(s) that can be either wired and/or wireless to connect the ultrasonic motor 1125 and the detector(s) 1135 with the arrangement 1130. A second scanner unit/arrangement may be provided which can have a second optical wedge 1150, a further mounting ring 1155, another magnetic ring 1160, another ultrasonic motor 1165 and position sensor array 1170, which are provided in the endoscopic head. A focusing lens 1175 can establish the resolution, working distance and working field diameter of the scanner, for example. The arrangement 1130 can be connected via a signal bus 1180 to an external scanner control, such as the computer control arrangement 130 illustrated in FIG. 1.

Figure 12B:
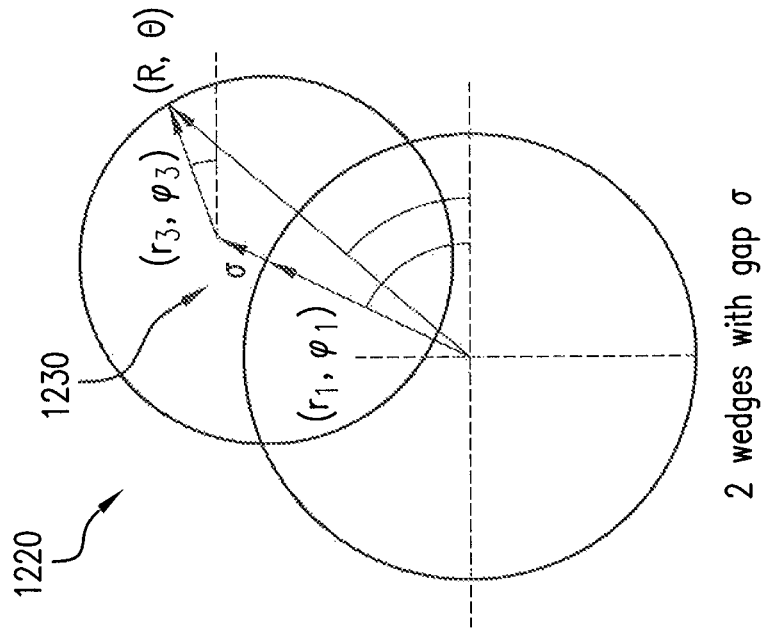
FIG. 12B is an illustration of an exemplary scanner geometry in accordance with another exemplary embodiment of the present disclosure.
Figure 12A:
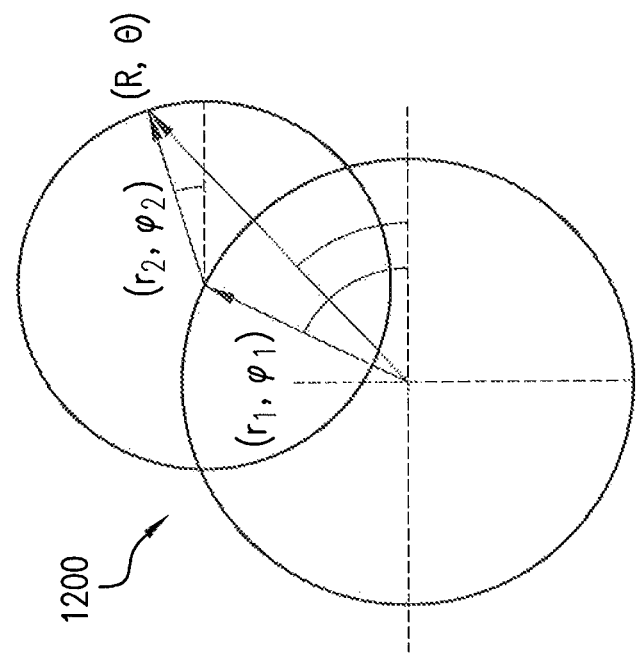
FIG. 12A is an illustration of an exemplary scanner geometry in accordance with an exemplary embodiment of the present disclosure.

FIG. 12A shows an illustration of a geometrical sketch 1200 representing a scanning pattern generated by an exemplary optical element and/or arrangement in accordance with an exemplary embodiment of the present disclosure, which can be based on an exemplary model. For example, the exemplary geometric sketch 1200 illustrated in FIG. 12A can be generated using the exemplary device, arrangement, system, apparatus, etc. according to the present disclosure that can include two or more optical elements, such as, e.g., optical elements 300, 310 illustrated in FIG. 3A, or an exemplary model thereof. The optical wedges and/or corresponding model that can be used to generate the geometrical sketch 1200 can include, e.g., two wedges 1110, 1150 shown in FIG. 11. Exemplary variables that can be used in a corresponding exemplary model are shown in FIG. 12A, for example.

FIG. 12B shows an exemplary geometrical sketch 1220 with the variables that can be used in a model in accordance with an exemplary embodiment of the present disclosure. The exemplary geometrical sketch 1220 can be the same or substantially similar to the geometrical sketch 1200 illustrated in FIG. 12A. It should be understood that the geometries and/or patterns used to generate and/or can be modeled by the two exemplary sketches 1200, 1220, respectively, can be different, as illustrated by a comparison of FIGS. 12A and 12B, for example. While the geometrical sketch 1220 illustrated in FIG. 12B can be generated by and/or represent the model of operation of the exemplary device that can be the same or substantially similar to the exemplary device used to generate the scanning pattern and/or be represented by the sketch 1200 (e.g., using two or more optical wedges), the geometries of the geometrical sketches 1200, 1220 with respect to the angles can be different from one another. For example, as illustrated in FIG. 12B, there can be a gap 1230 resulting from different angles, which can be modeled by the variable σ, representing the distance between the optical elements used to generate a scanning pattern corresponding to geometrical sketch 1220. As illustrated in FIG. 12A, in this exemplary embodiment, a gap 1230 does not exist and σ is not represented in the geometrical sketch 1200.

For example, the following exemplary equations can be used with a model in accordance with an exemplary embodiment of the present disclosure, such as the exemplary models corresponding to the exemplary sketches 1200, 1220 as illustrated in FIGS. 12A and 12B.

$$r_1 = (n_1 - 1) \times \beta_1$$
$$r_2 = (n_2 - 1) \times \beta_2$$
$$r_3 = \sqrt{r_2^2 - \sigma^2 \times \sin^2(\varphi_1 - \varphi_2)} - \sigma \times \cos(\varphi_1 - \varphi_2)$$
$$X = r_1 \times \cos\varphi_1 + \sigma \times \cos\varphi_1 + r_3 \times \cos\varphi_2$$
$$Y = r_1 \times \sin\varphi_1 + \sigma \times \sin\varphi_1 + r_3 \times \sin\varphi_2$$
$$R = \sqrt{X^2 + Y^2}$$
$$\theta = \begin{cases} a\tan(Y/X), & X > 0; \\ \pi + a\tan(Y/X), & X < 0 \end{cases}$$

where $r_1$ is the radial displacement from the axis. $\beta_1$ is the wedge angle, σ is the distance between the two wedges, R and θ are the radius and angle of target points in polar coordinates, X and Y are the positions in Cartesian coordinates, and $n_i$ is the refractive index of the wedges.

FIG. 13A is an exemplary image 1300 of an exemplary scanning pattern 1305 generated by a device in accordance with an exemplary embodiment of the present disclosure. To generate the exemplary scanning pattern 1305, an exemplary software arrangement (e.g., a set of computer-executable instruction) is provided that can be stored on a hardware computer-accessible medium which, when executed, configure a hardware processing arrangement to execute procedures to facilitate and/or control the operation of the exemplary system using optical devices via the controller to plot and trace an irradiation path corresponding to the scanning pattern 1305 illustrated in FIG. 13A.

For example, image 1305 can be a photograph of a trace made on a piece of thermal paper by a laser beam scanned and controlled by an exemplary device made and used in accordance with an exemplary embodiment of the present disclosure. The exemplary trace can be of a previously programmed path established in the computer control 130 illustrated in FIG. 1 and executed by the scanner control 135 illustrated in FIG. 1.

Provided herewith in the Appendix is exemplary code that can be used for performing an exemplary procedure in accordance with the present disclosure which can, e.g., generate the scanning pattern 1305 shown in the exemplary image 1300 of FIG. 13A.

For example, the exemplary procedures illustrated in the Appendix can be used with a $CO_2$ laser being delivered through a hollow core or photonic bandgap fiber. Such exemplary arrangement and/or system can be coupled with, e.g., a motor controller and industrial Zn—Se optics for $CO_2$ lasers. Certain exemplary motor control equations can be utilized via a computer software and/or programming language such as Matlab, for example. As described herein above, it is possible to use a fiber delivery configuration for the laser, as well as a direct laser delivery procedure.

According to such exemplary embodiment, the exemplary relationship between the desired points in the video image space and the rotational position of the optical elements can be represented by the following equations in a similar manner as described herein above with reference to FIG. 12A. For example, if $r_1 = r_2 = r$, the angles for each point (x,y) can be calculated by:

$$\varphi_1 = \theta - \cos^{-1}\left(\frac{R}{2r}\right) \quad \varphi_2 = \pi - 2\sin^{-1}\left(\frac{R}{2r}\right) \text{ where}$$
$$x = R\cos(\theta) \text{ and } y = R\sin(\theta).$$

For example, such exemplary equations (or functions) can provide absolute angles of each wedge for each point in a scanning pattern space, which can then be converted to relative angles that each wedge can rotate to obtain to the desired point from the previous point (e.g., to obtain an angle between 35° and 37°, a wedge can rotate about 2° from a starting point of 35°). According to the exemplary procedures of this exemplary embodiment of the present disclosure, the exemplary angles can then be verified by certain conditions to ensure that the shortest path is taken every time an wedge is rotated from one point to another point (e.g., to ensure that a wedge rotates −5° as opposed to 355°). The exemplary angles are then fed into the 'MotorRotateRelative' function (as illustrated in the exemplary code and procedures provided in the Appendix) which sends the motor rotation commands to an exemplary motor controller. Further details of the exemplary procedures and programming instructions are provided in enclosed Appendix, which include comments providing descriptions of the functions and commands used in accordance with certain exemplary embodiments of the present disclosure.

FIG. 13B shows an illustrations of an exemplary optical wedge or prism scanner 1310 which can be used in accordance with an exemplary embodiment of the present disclosure. As described herein above, the scanner in the exemplary system can include, e.g., two or more co-axial circular optical wedges and/or prisms that can each bend (refract) a laser beam or other light by an angle. This bend angle 1315 can depend on wedge parameters and wavelength of the laser or light, for example. For small angles, the relationship can be represented by, e.g., $\alpha \sim \phi n(\lambda)$ where $\alpha$ is the bend angle (known as the refracted angle), $\phi$ is the angle of the wedge or prism, and $n(\lambda)$ is the optical index of refraction of the wedge or prism material that can be dependent on the wavelength $\lambda$ of the light. For example, according to certain exemplary embodiments of the present disclosure, it is possible to use zinc selenide (ZnSe) as an optical material with an index of 2.34 at the 10.6 μm wavelength of a $CO_2$ laser.

FIG. 13C shows an illustration of a further exemplary scanning pattern 1320 in accordance with an exemplary embodiment of the present disclosure. For example, by rotating one wedge or prism, a light beam can be scanned in a circular motion at a fixed angle and, depending on the distance to the target, can generate a scanned circle 1321 having, e.g., a fixed diameter. If two or more wedges or prisms are used in series with one another, the light beam can be scanned over any point in a circular area 1325 with a diameter equal to twice the diameter of the scanned circle 1321 resulting from the single wedge scan, for example.

Figure 14:
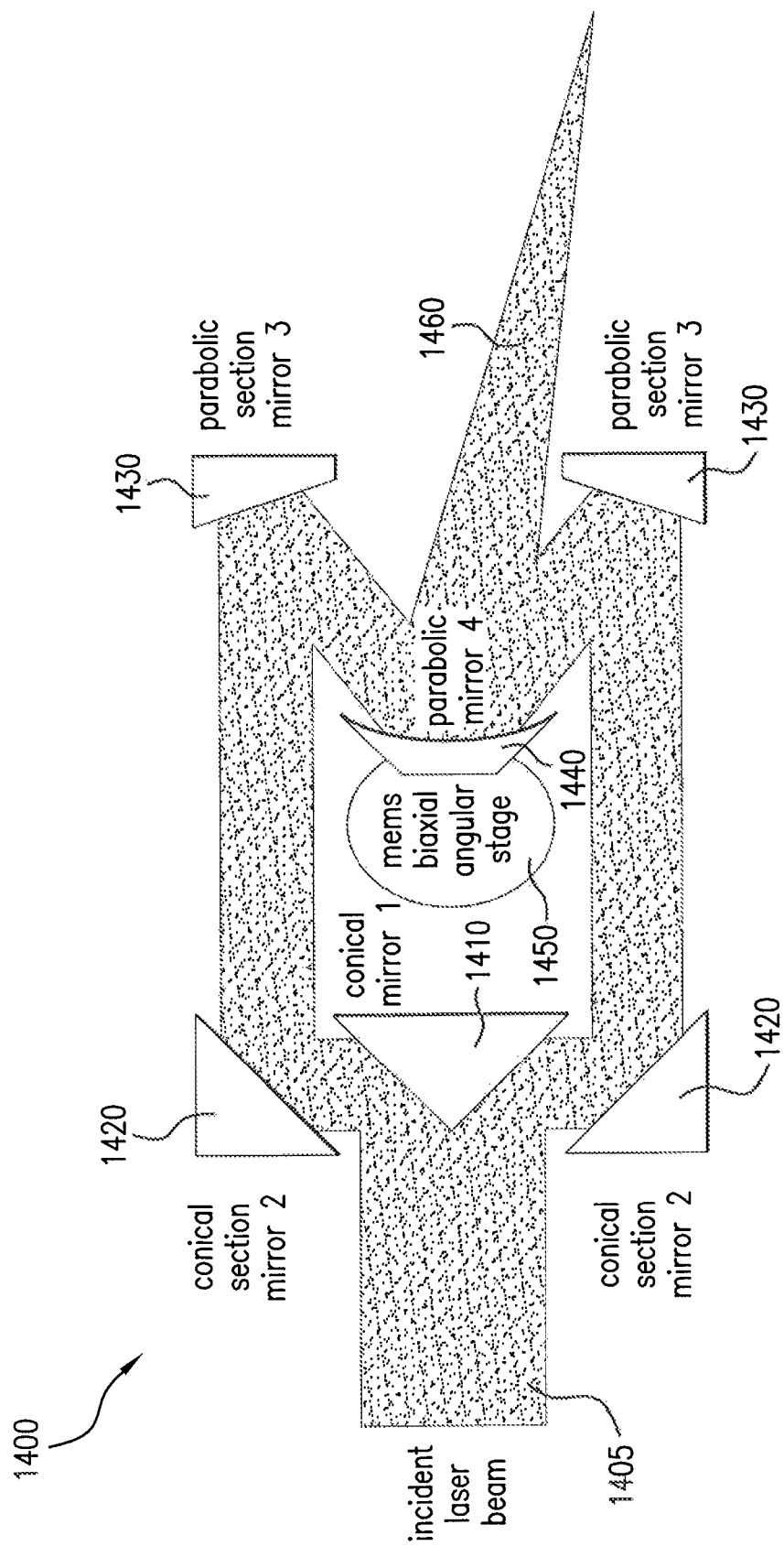
FIG. 14 is a side view of a device in accordance with a further exemplary embodiment of the present disclosure.

The first wedge can rotate the light beam by an angle $\phi 1$ to provide the light beam to the second prism, which can then produce a second angle $\phi 2$ for the light beam. If the two angles are equal and opposite from one another, then the light beam would provide little or no net angular change. If the angles are equal and oriented in the same direction as one another, the light beam will likely undergo double (or approximately double) the angular change of a single wedge. A characteristic of this type of the exemplary scanning system can be that the periphery of the corresponding scanned area can be uniquely defined by a single pair of angles. For example, every point in the circular area can be defined by two pairs of angles, and the center can be defined by infinite pairs of angles. Thus, to scan a straight line from one side of the circle, through the center and to the other side, the wedges can be moved simultaneously in opposite directions, for example. Such exemplary optical device/arrangement can be used for accurate optical alignment, and can be effectively and readily operated by a variety of motor and control systems, including, e.g., servo control and/or electromechanical motors and systems FIG. 14 shows a side view of another device/arrangement 1400 in accordance with a further exemplary embodiment of the present disclosure. As illustrated in FIG. 14, the exemplary device/arrangement 1400 can be used to expand an incident laser beam 1405 with a conical mirror 1410 and a conical section mirror 1420 into a wider hollow cylindrical (or tubular) beam of light, for example. The light beam can then be focused with a parabolic section mirror 1430 onto a parabolic mirror 1440, e.g., on the same or substantially the same axis with the incident laser beam 1405. The parabolic mirror 1440 can be mounted on a biaxial angular stage to control the direction of a reflected beam 1460. One of the advantages of the exemplary embodiment illustrated in FIG. 14 is that the exemplary device/arrangement 1400 can maintain a relatively small profile with respect to a relatively large aperture. For example, it is possible to utilize angular components of higher spatial frequencies without using central or low frequency components for a relatively large exemplary focused beam angular spectrum.

Figure 15:
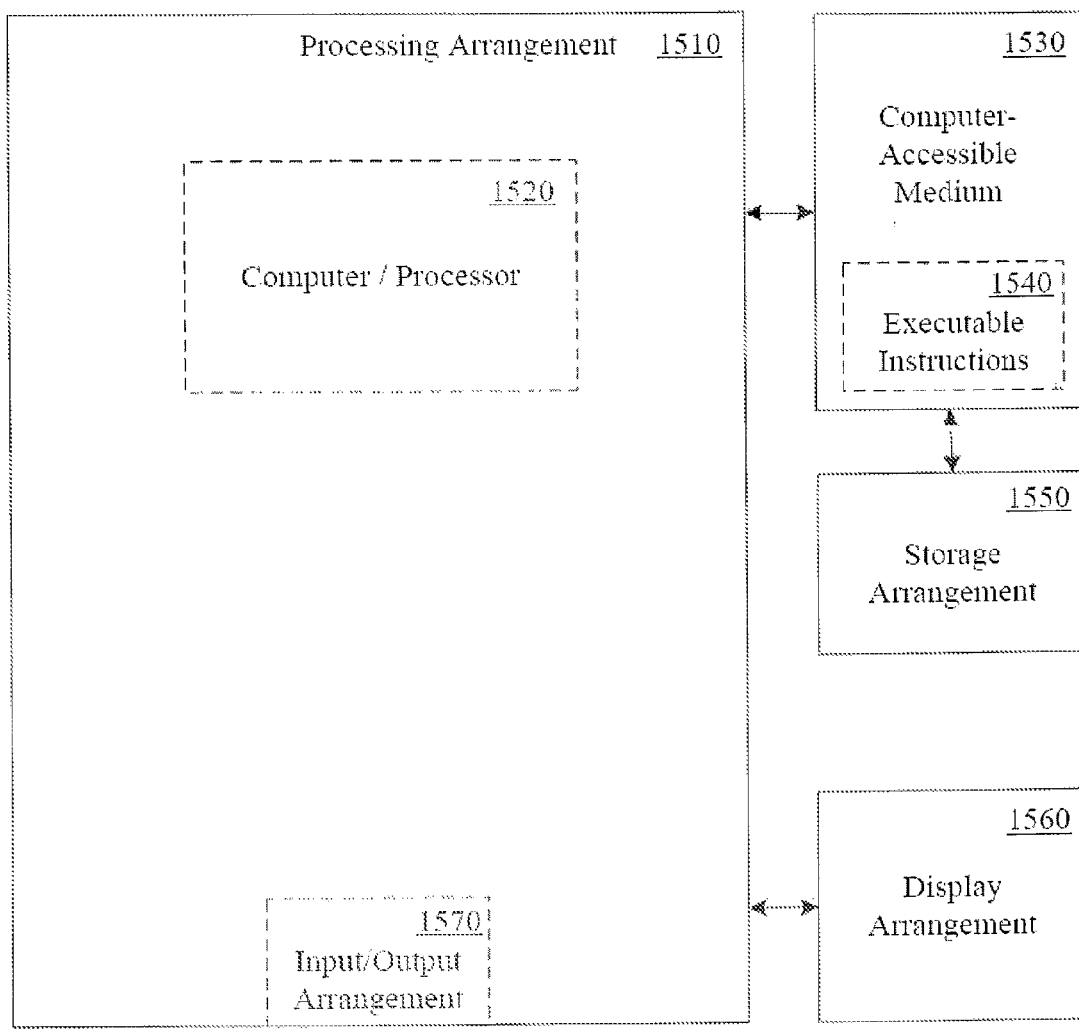
FIG. 15 is an illustration of a block diagram of a system in accordance with still another exemplary embodiment of the present disclosure.

FIG. 15 shows an exemplary block diagram of an exemplary embodiment of a system according to the present disclosure. For example, an exemplary procedure in accordance with the present disclosure can be performed by a processing arrangement and/or a computing arrangement 1510. Such processing/computing arrangement 1510 can be, e.g., entirely or a part of, or include, but not limited to, a computer/processor 1520 that can include, e.g., one or more microprocessors, and use instructions stored on a computer-accessible medium (e.g., RAM, ROM, hard drive, or other storage device).

As shown in FIG. 15, e.g., a computer-accessible medium 1530 (e.g., as described herein above, a storage device such as a hard disk, floppy disk, memory stick, CD-ROM, RAM, ROM, etc., or a collection/combination thereof) can be provided (e.g., in communication with the processing arrangement 1510). The computer-accessible medium 1530 can contain executable instructions 1540 thereon. In addition or alternatively, a storage arrangement 1550 can be provided separately from the computer-accessible medium 1530, which can provide the instructions to the processing arrangement 1510 so as to configure the processing arrangement to execute certain exemplary procedures, processes and methods, as described herein above, for example.

Further, the exemplary processing arrangement 1510 can be provided with or include an input/output arrangement 1570, which can include, e.g., a wired network, a wireless network, the internet, an intranet, a data collection probe, a sensor, etc. As shown in FIG. 15, the exemplary processing arrangement (computing arrangement) 1510 can be in communication with an exemplary display arrangement 1560, which, according to certain exemplary embodiments of the present disclosure, can be a touch-screen configured for inputting information to the processing arrangement in addition to outputting information from the processing arrangement, for example. Further, the exemplary display 1560 and/or a storage arrangement 1550 can be used to display and/or store data in a user-accessible format and/or user-readable format. The exemplary procedure described herein above can be performed using the exemplary system shown in FIG. 15 and described herein.

Figure 16:
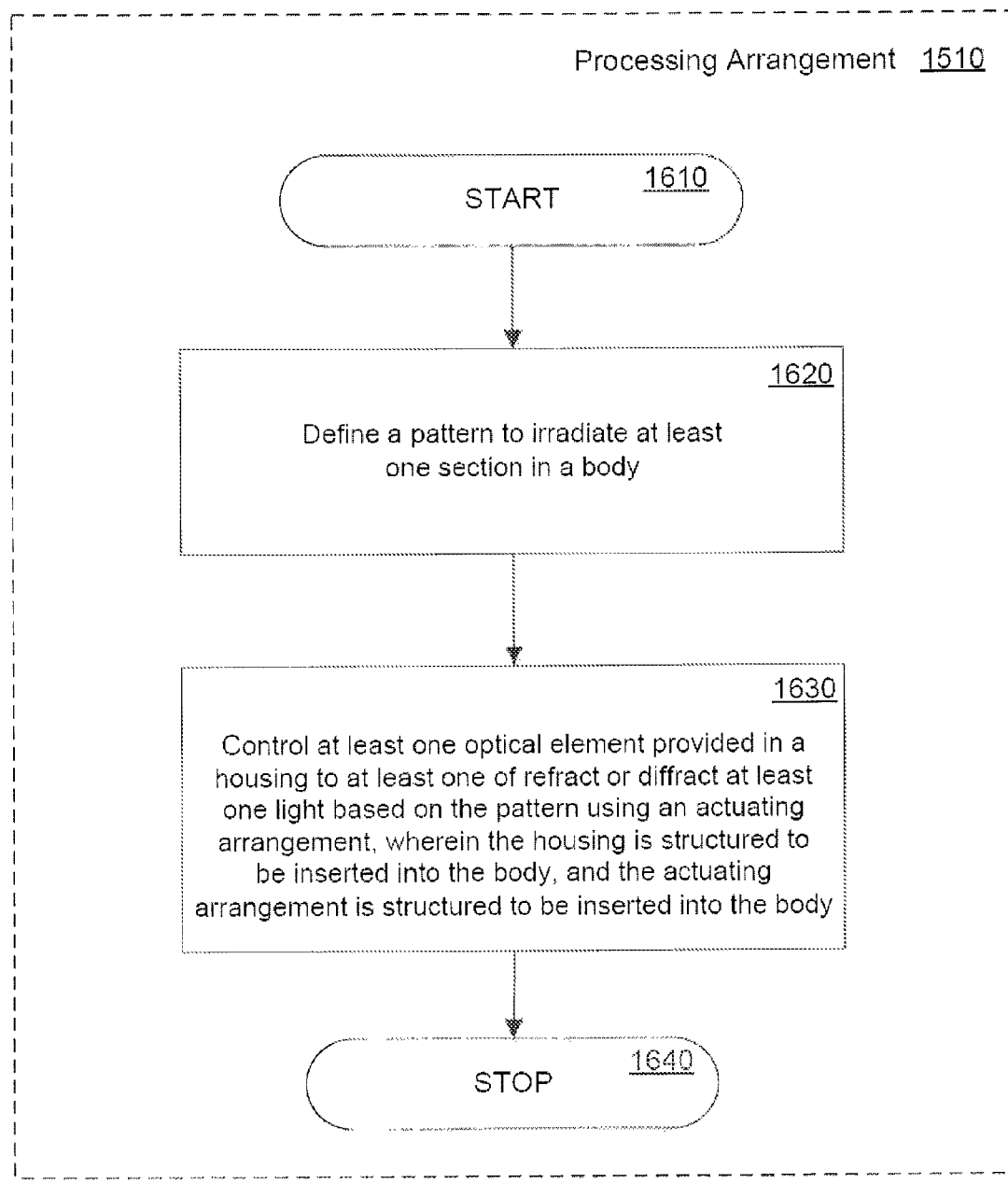
FIG. 16 is a flow diagram of an exemplary procedure in accordance with certain exemplary embodiments of the present disclosure.

FIG. 16 shows a flow diagram of a procedure in accordance with certain exemplary embodiments of the present disclosure. As shown in FIG. 16, the exemplary procedure can be executed on and/or by, e.g., the processing/computing arrangement 1510 of FIG. 15, and can be stored by a hardware computer-accessible medium, which can include the storage arrangement 1550 of FIG. 15. The processing/computing arrangement 1510 can be or included in the computer control 130 of FIG. 1, for example. The processing/computing arrangement 1510 can access the storage arrangement 1550 to obtain the instructions which can be used to configure the processing/computing arrangement 1510 to execute such exemplary procedure. For example, starting at subprocess 1610, in accordance with certain exemplary embodiments of the present disclosure, the exemplary processing/computing arrangement 1510 can, in subprocess 1620, define a pattern to irradiate at least one section in a body. In subprocess 1630, the exemplary processing/computing arrangement 1510 can control at least one optical element provided in a housing to refract and/or diffract light based on the pattern using an actuating arrangement. The housing and/or actuating arrangement can be structured to be inserted into the body, for example.

Figure 17:
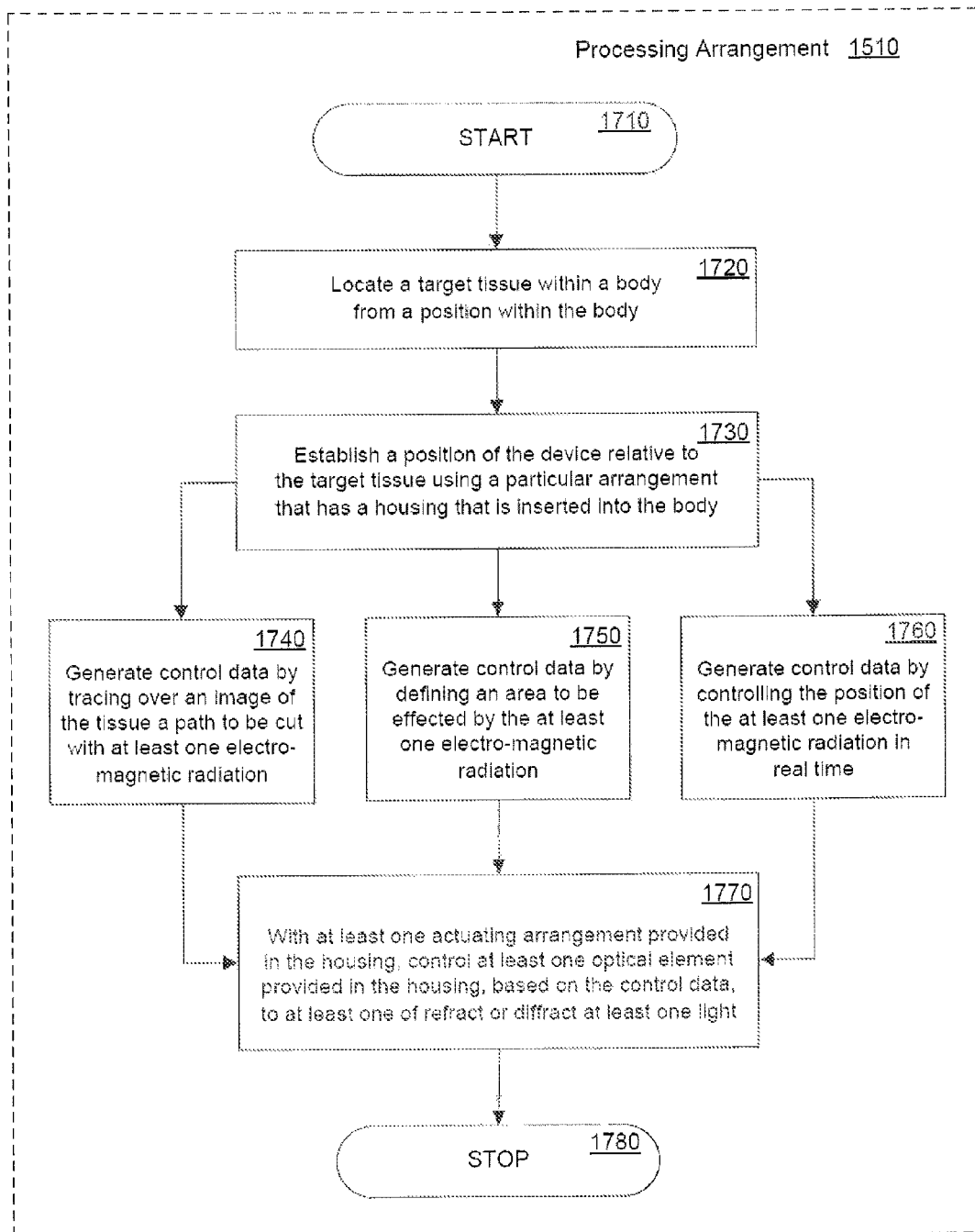
FIG. 17 is a flow diagram of an exemplary procedure in accordance with further exemplary embodiments of the present disclosure.

FIG. 17 shows a flow diagram of another procedure in accordance with certain exemplary embodiments of the present disclosure. As shown in FIG. 17, the exemplary procedure can be executed, at least in part, on and/or by, e.g., the processing/computing arrangement 1510 illustrated in FIG. 15, and can be stored by a hardware computer-accessible medium, which can include the storage arrangement 1550 of FIG. 15. The processing/computing arrangement 1510 can be or included in the computer control 130 of FIG. 1, for example. The processing/computing arrangement 1510 can access the storage arrangement 1550 to obtain the instructions which can be used to configure the processing/computing arrangement 1510 to execute such exemplary procedure.

For example, starting at subprocess 1710, a device (e.g., endoscope) in accordance with an exemplary embodiment of the present disclosure can locate target tissue within a body from a position within the body. In subprocess 1730, the exemplary processing/computing arrangement 1510 can establish a position of the device relative to the target tissue using a particular arrangement that has a housing that is inserted into the body, for example. Then, the exemplary processing/computing arrangement 1510 can generate control data by (i) tracing over an image of the tissue a path to be cut with at least one electro-magnetic radiation in subprocess 1740, (ii) defining an area to be effected by the at least one electro-magnetic radiation in subprocess 1750, and/or (iii) c controlling the position of the at least one electro-magnetic radiation in real time in subprocess 1760. The exemplary processing/computing arrangement 1510 can then, in subprocess 1770, with at least one actuating arrangement provided in the housing, control at least one optical element provided in the housing, based on the control data, to refract and/or diffract at least one light. The exemplary path can be based on a pattern in accordance with certain exemplary embodiments of the present disclosure, and the housing and/or actuating arrangement can be structured to be inserted into the body, for example.

Figure 18:
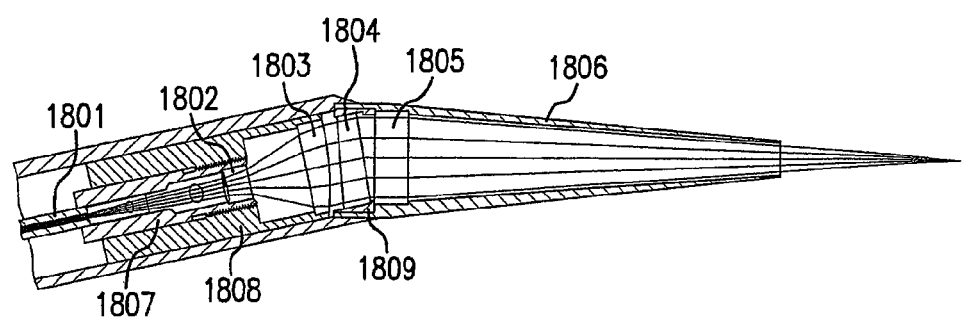
FIG. 18 is a side cross-sectional view of the endoscopic device in accordance with another exemplary embodiment of the present disclosure.

FIG. 18 shows a side cross-sectional view of the endoscopic device in accordance with another exemplary embodiment of the present disclosure. As shown in FIG. 18, with the exemplary endoscopic device shown therein, an electro-magnetic radiation (e.g., light) exiting a fiber optic 1801 or another light delivery device can be coupled to a negative expansion lens 1802 in a fiber-to-negative lens chuck 1807. The expending light being provided from the negative expansion lens 1802 can be collimated by a collimation lens 1803, which is maintained relative to the negative lens 1802 in a lens holder 1808. The collimated beam provided from the collimation lens 1803 can be deviated by a particular angle using a optical prism 1804 provided in a wedge holder 1809, and focused by a focusing lens 1805 through a delivery nozzle 1806 toward the sample or an anatomical structure.

Figure 19:
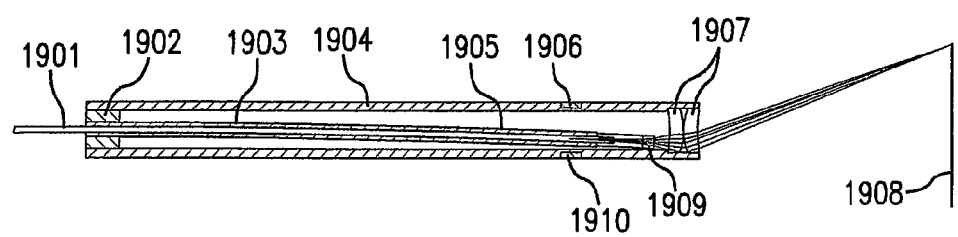
FIG. 19 is a side cross-sectional view of the endoscopic device in accordance with still another exemplary embodiment of the present disclosure.

FIG. 19 illustrates a side cross-sectional view of the endoscopic device in accordance with yet another exemplary embodiment of the present disclosure. For example, as provided in FIG. 19, using the exemplary endoscopic device shown therein, an optical fiber 1901 can be rigidly maintained in a flexible control tube 1903 that can be clamped using a clamp 1902 at one end of an outer tube 1904, which hold a pair of focusing lenses 1907 at a distal end of the outer tube 1904. The flexible control tube 1903 can rigidly maintain a negative expansion lens 1909 at a distal end of the flexible control tube 1903. The electro-magnetic radiation (e.g., light) exiting the fiber 1901 can be aligned and coupled to the negative expansion lens 1909. The distal end of the flexible control tube 1903 can be wrapped in an electrical coil 1905 with, e.g., wires running approximately parallel to the flexible control tube 1903. One or more aligned permanent magnets 1906 (e.g., which can be a pair of such magnets) can be placed around the electrical coil 1905. By varying the current in the electrical coil 1905, a displacement force can be generated on the flexible control tube 1903 to offset or move it from a center of the outer tube 1904. Such exemplary procedure can be used to position the optical fiber 1901 and the negative expansion lens 1909 relative to the focusing lenses 1907.

In yet another exemplary embodiment of the present disclosure, a further set (e.g., pair) of coils and magnets (not shown in FIG. 19 for the sake of clarity) can be placed orthogonal to the first set of the magnets 1906 and the coil 1905 to facilitate movement in the orthogonal direction. By varying the current in the coils, the radiation (e.g., beam) can be aimed to any position on the focal surface 1908 of the sample or structure. Alternatively, according to another exemplary embodiment of the present disclosure, the permanent magnets 1906 can be replaced or substituted with electromagnets, and/or the coil 1905 can be replaced substituted by, e.g., a permanent magnet tube. Exemplary motion can be achieved by varying the current in the electromagnets 1906. As described herein, the second set of the orthogonal electromagnets can be used to control the position in the orthogonal direction.

It should be understood that the exemplary system shown in FIG. 15 and described herein can be configured to perform the functionality described herein in exemplary embodiments illustrated in FIGS. 18 and 19. In addition, the exemplary methods and processes described herein with respect to the exemplary embodiments of FIGS. 18 and 19 can be performed by such exemplary system of FIG. 15.

Exemplary Applications

While the exemplary embodiment of the steering and focusing system/arrangement according to the present disclosure can be used to improve a minimally invasive surgical treatment of cancers of the head and neck, it is possible to use such exemplary systems/arrangements to treat diseases of other anatomical regions and to work with other types of laser wavelengths. Other exemplary areas of application can include laparoscopic, gastrointestinal, urologic and thoracoscopic minimally invasive surgery The foregoing merely illustrates the principles of the disclosure. Various modifications and alterations to the described embodiments will be apparent to those skilled in the art in view of the teachings herein, and especially in the appended claims. It will thus be appreciated that those skilled in the art will be able to devise numerous systems, arrangements, and methods which, although not explicitly shown or described herein, embody the principles of the disclosure and are thus within the spirit and scope of the disclosure. In addition, all publications and references referred to above are incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement which can be a microprocessor, mini, macro, mainframe, etc. In addition, to the extent that the prior art knowledge has not been explicitly incorporated by reference herein above, it is explicitly being incorporated herein in its entirety. All publications referenced above are incorporated herein by reference in their entireties.

APPENDIX

I. Script file used to entirely run the system by setting parameters, defining the desired laser path, and sending the necessary commands to each motor. Calls the various functions listed on the following pages. (ControlMotorMASTER.m).

APPENDIX-continued

```
clc; clear all; close all
% matlab function to reset serial port
instrreset
s=serial('com1', 'Terminator', 'CR'):
fopen(s);
% Stefan's TMCM-310 initialization routine
MotorInitialization(s)
% pause prevents serial port from choking
pause(0.05)
% Stefan's TMCM-310 homing routine
MotorHome(s)
pause(0.05)
% % Defining triangle path for laser to follow:
% % Change "k" value in loop below to 121 when using this smaller triangle
% x(1:30)=[-3:0.1:-0.1];
% x(31:60)=[0:0.1:2.9];
% x(61:121)=fliplr([-3:0.1:3]);
% y(1:30)=[-1.5:0.1:1.4];
% y(31.60)=fliplr([-1.4:0.1:1.5]);
% y(61:121)=-1.5;
% % plotting triangular path for reference
% % plot(x,y)
% Change "k" value in loop below la 201 when using this larger triangle
x(1:50)=[-5:0.1:-0.1];
x(51:100)=[0:0.1:4.9];
x(101:201)=fliplr([-5:0.1:5]);
y(1:50)=[-2.5:0.1:2.4];
y(51:100)=fliplr([-2.4:0.1:2.5]);
y(101:201)=-2.5;
% plotting triangular path for reference
% plot(x,y)
% as homing switches are set to 12 o'clock, we move wedges to
% center point and call that 0 degrees for both
MotorRotateRelative(s,-90,-90);
absth1=(0.9*round((-90/0.9)*-4.2857)/-4.2857)+90;
absth2=absth1;
% defining maximum radius of each circle (2*r is the maximum radius for the
% two combined circles)-NOTE: This will later need to change to a function
% of the distance from the wedges to the target plane.
r=3;
% now we move the wedges to the desired points
% NOTE: change the max k value to match the number of points in the
% triangle defined above
for k=1:201
        if sqrt(x(k)^2+y(k)^2)<=2*r % check to make sure inside the field
            % For testing purposes, show x and y values.
            % X=x(k)
            % Y=y(k)
            % convert points to angles with our own conversion function
            [th1 th2]=xy2th1th2(x(k),y(k),r);
            % Setting conditions to pick shortest path
            rotth1=th1-absth1;
            rotth2=th2-absth2;
            if rotth1>180
                rotth1=rotth1-360;
            elseif rotth1<(-180)
                rotth1=rotth1+360;
            end
            if rotth2>180
                rotth2=rotth2-360;
            elseif rotth2<(-180)
                rotth2=rotth2+360;
            end
            % Stefan's move wedges function
            [relth1 relth2]=MotorRotateRelative(s,rotth1,rotth2);
            % update current angular position
            absth1=absth1+relth1;
            absth2=absth2+relth2;
            % Pause to allow 2nd motor to reach its desired point before the
            % first motor starts rotating to the next point
            pause(0.1)
        else
            'out of range'
        end
end
```

II. Motor initialization function to set motor parameters. Sends commands to the motor driver/controller. (MotorInitialization.m):

```
function [ ] = MotorInitialization(s)
%Motor Settings Function
MC0=['ASAP 6, 0, 400' 13]; %Max Current to Motors 0 and 1 (0.8A)
```

APPENDIX-continued

```
        MC1=['ASAP 6, 1, 400' 13];
        MPS0=['ASAP 4, 0, 50' 13]; %Max Positioning Speed for Motors 0 and 1
        MPS1=['ASAP 4, 1, 50' 13];
        MSR0=['ASAP 140, 0, 1' 13]; %Microstep Resolution for Motors 0 and 1 - Half-stepped
        MSR1=['ASAP 140, 1, 1' 13];
            for a=1:length(MC0)
                fwrite(s,int8(MC0(a)))
            end
            out=fscanf(s);
            out=fscanf(s);
            pause(0.05)
            for b=1:length(MC1)
                fwrite(s,int8(MC1(b)))
            end
            out=fscanf(s);
            out=fscanf(s);
            pause(0.05)
            for c=1:length(MPS0)
                fwrite(s,int8(MPS0(c)))
            end
            out=fscanf(s);
            out=fscanf(s);
            pause(0.05)
            for d=1:length(MPS1)
                fwrite(s,int8(MPS1(d)))
            end
            out=fscanf(s);
            out=fscanf(s);
            pause(0.05)
            for e=1:length(MSR0)
                fwrite(s,int8(MSR0(e)))
            end
            out=fscanf(s);
            out=fscanf(s);
            pause(0.05)
            for f=1:length(MSR1)
                fwrite(s,int8(MSR1(f)))
            end
            out=fscanf(s);
            out=fscanf(s);
            pause(0.05)
III.    Motor homing function which zeros the motor position. (MotorHome.m)
            function [ ]=MotorHome(s)
            % Motor Homing Function for TMCM-300
            % For limit: switches connected with NC terminal to 'L' and
            % common terminal to 'GND' on the TMCM-310 board
            % create reference search start strings
            RFS0a=['ARFS START, 0' 13];
            RFS1a=['ARFS START, 1' 13];
            % create reference search status strings
            RFS0b=['ARFS STATUS, 0' 13];
            RFS1b=['ARFS STATUS, 1' 13];
            % create end condition string
            endcondition=int8(['BA 100 8' 13]);
            % send the refernce search start commands and clear replies
            for a=1:length(RFS0a)
                fwrite(s,int8(RFS0a(a)))
            end
            out=fscanf(s);
            out=fscanf(s);
            pause(0.05)
            for a=1:length(RFS1a)
                fwrite(s,int8(RFS1a(a)))
            end
            out=fscanf(s);
            out=fscanf(s);
            pause(0.05)
            % send the reference search start commands and get replies
            for a=1:length(RFS0b)
                fwrite(s,int8(RFS0b(a)))
            end
            outCOM0=int8(fscanf(s));
            outRET0=int8(fscanf(s));
            pause(0.05)
            for a=1:length(RFS1b)
                fwrite(s,int8(RFS1b(a)))
            end
            outCOM1=int8(fscanf(s));
            outRET1=int8(fscanf(s));
            pause(0.05)
```

APPENDIX-continued

```
    % compare replies to endcondition
    while outRET0(8)~=48
        for a=1:length(RFS0b)
            fwrite(s,int8(RFS0b(a)))
        end
        outCOM0=int8(fscanf(s));
        outRET0=int8(fscanf(s));
        pause(0.05)
    end
    while outRET1(8)~=48
        for a=1:length(RFS1b)
            fwrite(s,int8(RFS1b(a)))
        end
        outCOM1=int8(fscanf(s));
        outRET1=int8(fscanf(s));
        pause(0.05)
    end
```

IV. Motor relative rotation function that sends the necessary commands to move each motor relative to its current position. (MotorRotateRelative.m)

```
    function [realth1, realth2]=MotorRotateRelative(s, theta1, theta2)
    %Function to rotate motor by an angular ammount
    % s is the serial port object.
    % theta1 and theta2 are the angles
    %Define Command Strings to send to TMCM-310
    % convert angles to half steps - (0.9 is half stepped)
    % the fraction 4.2857 is the ratio between the two pulleys
    steps1=round((theta1/0.9)*(-60/14));
    steps2=round((theta2/0.9)*(60/14));
    outstr0=['AMVP REL, 0, ' int2str(steps1) 13];
    outstr1=['AMVP REL, 1, ' int2str(steps2) 13];
    realth1=steps1*0.9/(-60/14);
    realth2=steps2*0.9/(60/14);
    %Writing Relative Positioning Strings to TMCM-310
    for i=1:length(outstr0)
        fwrite(s,int8(outstr0(i)))
    end
    %The following returns are necessary in order for the homing function
    %to work properly. This is because the sent and returned strings build up
    %and must be scanned after each command in order to get the return string
    %corresponding to each command.
    out=fscanf(s);
    out=fscanf(s);
    pause(0.05) %The pause is necessary in order for the board to accept both commands
    without error.
    for j=1:length(outstr1)
        fwrite(s,int8(outstr1(j)))
    end
    out=fscanf(s);
    out=fscanf(s);
    pause(0.05)
```

V. Function to convert (x,y) point to angles of rotation for each wedge. (xy2th1th2.m)

```
    % This function converts the input 'x' and 'y' co-ordinates to angles theta1
    % and theta2. This program always gives the value of the angle from the
    % position it is at, i.e. considering that point as the origin.
    function [theta1,theta2]=xy2th1th2(x,y,r)
    n=sqrt((x^2)+(y^2));
    if n<=(2*r)
        %The value of variable b and the formula for theta1 and theta2 was
        %mathematically calculated.
        b = acosd(sqrt(x^2+y^2)/(2*r));
        theta1 = ((atan2(y,x)*180)/pi)+ b;
        theta2 = ((atan2(y,x)*180)/pi)- b;
    else
        theta1=('The values of x and y are out of the maneuvering limits')
        theta2=('The values of x and y are out of the maneuvering limits')
    end
```

What is claimed is:

1. An endoscopic laser scalpel system, comprising:
a surgical laser source providing laser light for at least one of incision, excision, and ablation of tissue in minimally invasive surgery;
a laryngoscope or endoscope having a distal end to be inserted into a body cavity to deliver the laser light to a target tissue therein; and
an endoscopic head mounted on the distal end of the laryngoscope or endoscope, the endoscopic head comprising:
   an expansion lens positioned to expand the laser light from the laser source;
   a collimating lens positioned to collimate the laser light from the expansion lens;
   a focusing lens interfacing the endoscopic head to the body cavity; and
   at least two rotatable optical elements positioned between the collimating lens and the focusing lens, each of which comprises an optical wedge or prism configured to refract light or a diffraction grating configured to diffract light,
wherein the rotatable optical elements and the lenses are aligned with their centers on a common optical axis, and each of the optical elements is configured to rotate about the optical axis,
wherein the rotatable optical elements are each structured to receive incident laser light at a first elevation angle with respect to the optical axis, and generate refracted or diffracted laser light at a second elevation angle which is different from the first elevation angle with respect to the optical axis, and
wherein the refracted or diffracted laser light is generated with a second rotation angle around the optical axis that is dependent on a first rotation angle of the respective rotatable optical element around the optical axis.

2. The endoscopic laser scalpel system according to claim 1, wherein the laser source comprises an optical waveguide.

3. The endoscopic laser scalpel system according to claim 1, wherein the at least two rotatable optical elements comprise a Risley prism pair.

4. The endoscopic laser scalpel system according to claim 1, wherein the diffraction grating (a) has a variable pitch and comprises an acousto-optical device or a liquid crystal device, or (b) has a fixed pitch.

5. The endoscopic laser scalpel system according to claim 2, wherein the optical wave guide is a hollow core or photonic bandgap optical fiber.

6. The endoscopic laser scalpel system according to claim 1, further comprising at least two actuating arrangements each configured to rotate the respective optical elements around the optical axis to change the second rotation angle of the refracted or diffracted laser light, each actuating arrangement comprising a mounting ring to which the respective optical element is mounted, a magnetic ring attached to the mounting ring, at least one sensor to measure the position of the magnetic ring, and a motor to rotate the mounting ring.

7. The endoscopic laser scalpel system according to claim 4, wherein the diffraction grating of fixed pitch comprises a holographic transmission grating or a blazed grating.

* * * * *

UNITED STATES PATENT AND TRADEMARK OFFICE
CERTIFICATE OF CORRECTION

PATENT NO. : 9,554,857 B2
APPLICATION NO. : 13/420340
DATED : January 31, 2017
INVENTOR(S) : Ricardo Toledo-Crow, Snehal Patel and Milind Rajadhyaksha It is certified that error appears in the above-identified patent and that said Letters Patent is hereby corrected as shown below:

In the Specification

Column 1, Line 12, the portion reading ". The present application also relates to and" should read --, which--

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*